(12) United States Patent
Rabinovitz et al.

(10) Patent No.: US 8,515,507 B2
(45) Date of Patent: Aug. 20, 2013

(54) DEVICE AND METHOD FOR DETECTING IN-VIVO PATHOLOGY

(75) Inventors: Elisha Rabinovitz, Haifa (IL); Osnat Sella-Tavor, Kfar Kish (IL); Amit Pascal, Haifa (IL); Noam Emanuel, Jerusalem (IL)

(73) Assignee: Given Imaging Ltd., Yoqneam (IL)

( * ) Notice: Subject to any disclaimer, the term of this patent is extended or adjusted under 35 U.S.C. 154(b) by 1025 days.

(21) Appl. No.: 12/485,665

(22) Filed: Jun. 16, 2009

(65) Prior Publication Data

US 2009/0312631 A1    Dec. 17, 2009

Related U.S. Application Data

(60) Provisional application No. 61/061,746, filed on Jun. 16, 2008, provisional application No. 61/090,123, filed on Aug. 19, 2008, provisional application No. 61/159,260, filed on Mar. 11, 2009.

(51) Int. Cl.
*A61B 5/1455* (2006.01)

(52) U.S. Cl.
USPC .................... 600/310; 600/476; 600/160

(58) Field of Classification Search
USPC ............. 600/309, 310, 317, 322, 341, 473, 600/476, 109, 160
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,017,261 A | 4/1977 | Svoboda et al. | |
| 4,027,510 A | 6/1977 | Hiltebrandt | |
| 4,038,485 A | 7/1977 | Johnston et al. | |
| 4,177,800 A | 12/1979 | Enger | |
| 4,198,960 A | 4/1980 | Utsugi | |
| 4,239,040 A | 12/1980 | Hosoya et al. | |
| 4,246,784 A | 1/1981 | Bowen | |
| 4,278,077 A | 7/1981 | Mizumoto | |
| 4,306,877 A | 12/1981 | Lubbers | |
| 4,337,222 A | 6/1982 | Kitajima et al. | |
| 4,431,005 A | 2/1984 | McCormick | |
| 4,439,197 A | 3/1984 | Honda et al. | |
| 4,646,724 A | 3/1987 | Sato et al. | |

(Continued)

FOREIGN PATENT DOCUMENTS

| | | |
|---|---|---|
| DE | 34 40 177 | 6/1986 |
| EP | 0 344 770 | 12/1989 |

(Continued)

OTHER PUBLICATIONS

High Throughput Microchannel DNA Sequencer, Mar. 15, 2000.

(Continued)

*Primary Examiner* — Eric Winakur

(74) *Attorney, Agent, or Firm* — Pearl Cohen Zedek Latzer, LLP

(57) ABSTRACT

Devices, systems and methods for detecting in vivo pathology are provided. An in vivo sensing device comprises a reacting layer with at least one type of binding agent attached thereon, a sensor configured for sensing an optical change occurring on the reacting substrate, and at least one illumination source. In-vivo fluids are in constant contact with the reacting substrate so that in vivo marker indicating pathology may bind to the binding agent attached onto the reacting layer and may be viewed by the sensor.

17 Claims, 18 Drawing Sheets

(56) References Cited

U.S. PATENT DOCUMENTS

| | | |
|---|---|---|
| 4,689,621 A | 8/1987 | Kleinberg |
| 4,741,327 A | 5/1988 | Yabe |
| 4,784,155 A | 11/1988 | Mills |
| 4,803,992 A | 2/1989 | Lemelson |
| 4,817,632 A | 4/1989 | Schramm |
| 4,819,620 A | 4/1989 | Okutsu |
| 4,844,076 A | 7/1989 | Lesho et al. |
| 4,885,077 A | 12/1989 | Karakelle et al. |
| 4,915,113 A | 4/1990 | Holman |
| 4,920,045 A | 4/1990 | Okuda et al. |
| 4,936,823 A | 6/1990 | Colvin et al. |
| 4,994,029 A | 2/1991 | Rohrbough |
| 5,006,314 A | 4/1991 | Gourley et al. |
| 5,042,486 A | 8/1991 | Pfeiler et al. |
| 5,081,040 A | 1/1992 | Patel et al. |
| 5,088,492 A | 2/1992 | Takayama et al. |
| 5,096,671 A | 3/1992 | Kane et al. |
| 5,109,870 A | 5/1992 | Silny et al. |
| 5,114,864 A | 5/1992 | Walt |
| 5,187,572 A | 2/1993 | Nakamura et al. |
| 5,211,165 A | 5/1993 | Dumoulin et al. |
| 5,224,467 A | 7/1993 | Oku |
| 5,252,494 A | 10/1993 | Walt |
| 5,267,033 A | 11/1993 | Hoshino |
| 5,279,607 A | 1/1994 | Schentag et al. |
| 5,306,623 A | 4/1994 | Kiser et al. |
| 5,311,858 A | 5/1994 | Adair |
| 5,330,427 A | 7/1994 | Weissenburger |
| 5,362,478 A | 11/1994 | Desai et al. |
| 5,368,027 A | 11/1994 | Lubbers et al. |
| 5,373,840 A | 12/1994 | Knighton |
| 5,376,336 A | 12/1994 | Lubbers et al. |
| 5,381,784 A | 1/1995 | Adair |
| 5,385,846 A | 1/1995 | Kuhn et al. |
| 5,395,366 A | 3/1995 | D'Andrea et al. |
| 5,398,670 A | 3/1995 | Ortiz et al. |
| 5,429,132 A | 7/1995 | Guy et al. |
| 5,443,701 A | 8/1995 | Willner et al. |
| 5,447,868 A | 9/1995 | Augurt |
| 5,460,969 A | 10/1995 | Fielder et al. |
| 5,479,935 A | 1/1996 | Essen-Moller |
| 5,490,969 A | 2/1996 | Bewlay et al. |
| 5,495,114 A | 2/1996 | Adair |
| 5,558,640 A | 9/1996 | Pfeiler et al. |
| 5,563,071 A | 10/1996 | Augurt |
| 5,582,170 A | 12/1996 | Soller |
| 5,604,531 A | 2/1997 | Iddan et al. |
| 5,653,677 A | 8/1997 | Okada et al. |
| 5,681,279 A | 10/1997 | Roper et al. |
| 5,697,384 A | 12/1997 | Miyawaki et al. |
| 5,762,770 A | 6/1998 | Pritchard et al. |
| 5,800,350 A | 9/1998 | Coppleson et al. |
| 5,814,525 A | 9/1998 | Renschler et al. |
| 5,819,736 A | 10/1998 | Avny et al. |
| 5,833,602 A | 11/1998 | Osemwota |
| 5,833,603 A | 11/1998 | Kovacs et al. |
| 5,837,196 A | 11/1998 | Pinkel et al. |
| 5,853,005 A | 12/1998 | Scanlon |
| 5,892,144 A | 4/1999 | Meller et al. |
| 5,904,647 A | 5/1999 | Ouchi |
| 5,913,820 A | 6/1999 | Bladen et al. |
| 5,916,176 A | 6/1999 | Caillouette |
| 5,929,901 A | 7/1999 | Adair et al. |
| 5,932,480 A | 8/1999 | Maruo et al. |
| 5,968,765 A | 10/1999 | Grage et al. |
| 5,983,120 A * | 11/1999 | Groner et al. ............ 600/310 |
| 5,986,693 A | 11/1999 | Adair et al. |
| 5,993,378 A | 11/1999 | Lemelson |
| 6,006,121 A | 12/1999 | Vantrappen et al. |
| 6,043,839 A | 3/2000 | Adair et al. |
| 6,074,349 A | 6/2000 | Crowley |
| 6,099,482 A | 8/2000 | Brune et al. |
| 6,115,061 A | 9/2000 | Lieberman et al. |
| 6,123,683 A | 9/2000 | Propp |
| 6,149,581 A | 11/2000 | Klingenstein |
| 6,162,469 A | 12/2000 | Atarashi |
| 6,165,128 A | 12/2000 | Céspedes et al. |
| 6,172,640 B1 | 1/2001 | Durst et al. |
| 6,185,443 B1 | 2/2001 | Crowley |
| 6,188,355 B1 | 2/2001 | Gilboa |
| 6,233,476 B1 | 5/2001 | Strommer et al. |
| 6,240,312 B1 | 5/2001 | Alfano et al. |
| 6,256,522 B1 | 7/2001 | Schultz |
| 6,285,897 B1 | 9/2001 | Kilcoyne et al. |
| 6,330,464 B1 | 12/2001 | Colvin et al. |
| 6,330,465 B1 | 12/2001 | Huyberechts et al. |
| 6,369,812 B1 | 4/2002 | Iyriboz et al. |
| 6,395,562 B1 | 5/2002 | Hammock et al. |
| 6,475,145 B1 | 11/2002 | Baylor |
| 6,488,694 B1 | 12/2002 | Lau et al. |
| 6,498,941 B1 | 12/2002 | Jackson |
| 6,584,348 B2 | 6/2003 | Glukhovsky |
| 6,607,301 B1 | 8/2003 | Glukhovsky et al. |
| 6,632,171 B2 | 10/2003 | Iddan et al. |
| 6,692,430 B2 | 2/2004 | Adler |
| 6,776,165 B2 | 8/2004 | Jin |
| 6,934,573 B1 | 8/2005 | Glukhovsky et al. |
| 6,950,690 B1 | 9/2005 | Meron et al. |
| 7,118,529 B2 | 10/2006 | Glukhovsky et al. |
| 7,468,044 B2 | 12/2008 | Iddan |
| 7,727,169 B1 | 6/2010 | Lewkowicz et al. |
| 7,857,767 B2 * | 12/2010 | Ferren et al. .............. 600/309 |
| 7,901,366 B2 | 3/2011 | Iddan |
| 2001/0031502 A1 | 10/2001 | Watson, Jr. et al. |
| 2001/0034025 A1 | 10/2001 | Modlin et al. |
| 2001/0035902 A1 | 11/2001 | Iddan et al. |
| 2001/0045899 A1 | 11/2001 | Hoek |
| 2001/0051766 A1 | 12/2001 | Gazdzinski |
| 2001/0053535 A1 | 12/2001 | Bashir et al. |
| 2002/0001695 A1 | 1/2002 | Tajima et al. |
| 2002/0015952 A1 | 2/2002 | Anderson et al. |
| 2002/0042562 A1 | 4/2002 | Meron et al. |
| 2002/0103417 A1 | 8/2002 | Gazdzinski |
| 2002/0111544 A1 * | 8/2002 | Iddan ........................ 600/310 |
| 2002/0146368 A1 | 10/2002 | Meron et al. |
| 2002/0158976 A1 | 10/2002 | Vni et al. |
| 2002/0173718 A1 | 11/2002 | Frisch et al. |
| 2002/0177779 A1 | 11/2002 | Adler et al. |
| 2002/0198439 A1 | 12/2002 | Mizuno |
| 2003/0018280 A1 | 1/2003 | Lewcowicz et al. |
| 2003/0020810 A1 | 1/2003 | Takizawa et al. |
| 2003/0023150 A1 | 1/2003 | Yokoi et al. |
| 2003/0028078 A1 | 2/2003 | Glukhovsky |
| 2003/0045790 A1 | 3/2003 | Lewkowicz et al. |
| 2003/0114742 A1 | 6/2003 | Lewkowicz et al. |
| 2003/0139647 A1 | 7/2003 | Raz et al. |
| 2003/0139661 A1 | 7/2003 | Kimchy et al. |
| 2003/0167000 A1 | 9/2003 | Mullick et al. |
| 2003/0195400 A1 | 10/2003 | Glukhovsky |
| 2003/0195415 A1 | 10/2003 | Iddan |
| 2003/0208107 A1 | 11/2003 | Refael |
| 2003/0214579 A1 | 11/2003 | Iddan |
| 2003/0214580 A1 | 11/2003 | Iddan |
| 2003/0216622 A1 | 11/2003 | Meron et al. |
| 2004/0092825 A1 | 5/2004 | Madar et al. |
| 2004/0109488 A1 | 6/2004 | Glukhovsky et al. |
| 2005/0137468 A1 | 6/2005 | Avron et al. |
| 2006/0058683 A1 * | 3/2006 | Chance ...................... 600/476 |

FOREIGN PATENT DOCUMENTS

| | | |
|---|---|---|
| EP | 0 693 271 | 1/1996 |
| EP | 0 945 102 | 9/1999 |
| EP | 1 002 229 | 1/2004 |
| FR | 2 688 997 | 10/1993 |
| IL | 143259 | 5/2001 |
| JP | 57-45833 | 3/1982 |
| JP | 1107737 | 4/1989 |
| JP | 3-289779 | 12/1991 |
| JP | 4-109927 | 4/1992 |
| JP | 4144533 | 5/1992 |
| JP | 4-180736 | 6/1992 |
| JP | 6063051 | 8/1992 |
| JP | 5015515 | 1/1993 |
| JP | 5200015 | 8/1993 |

| | | |
|---|---|---|
| JP | 6114037 | 4/1994 |
| JP | 6285044 | 10/1994 |
| JP | 7111985 | 5/1995 |
| JP | 7275197 | 10/1995 |
| JP | 2000506410 | 9/1998 |
| JP | 2001224553 | 2/2000 |
| JP | 2000-342522 | 12/2000 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001231744 | 8/2001 |
| JP | 2001245844 | 9/2001 |
| JP | 2002-010990 | 12/2001 |
| JP | 2000342524 | 6/2002 |
| JP | 2000342525 | 6/2002 |
| WO | WO 92/21307 | 12/1992 |
| WO | WO 97/33513 | 9/1997 |
| WO | WO 97/45720 | 12/1997 |
| WO | WO 98/07366 | 2/1998 |
| WO | WO 98/11816 | 3/1998 |
| WO | WO 99/11754 | 3/1999 |
| WO | WO 99/32028 | 7/1999 |
| WO | WO 00/13003 | 3/2000 |
| WO | WO 00/22975 | 4/2000 |
| WO | WO 01/07919 | 2/2001 |
| WO | WO 01/08548 | 2/2001 |
| WO | WO 01/25481 | 4/2001 |
| WO | WO 01/50941 | 7/2001 |
| WO | WO 01-50941 | 7/2001 |
| WO | WO 01/53792 | 7/2001 |
| WO | WO 01/65995 | 9/2001 |
| WO | WO 01/69212 | 9/2001 |
| WO | WO 02/054932 | 7/2002 |
| WO | WO 02/55126 | 7/2002 |
| WO | WO 02/55984 | 7/2002 |
| WO | WO 02/094337 | 11/2002 |
| WO | WO 03/003706 | 1/2003 |
| WO | WO 03/005877 | 1/2003 |
| WO | WO 03/011103 | 2/2003 |
| WO | WO 03/094723 | 11/2003 |
| WO | WO 2004/004540 | 1/2004 |
| WO | WO 2004/028336 | 4/2004 |
| WO | WO 2004/035106 | 4/2004 |
| WO | WO 2004/045395 | 6/2004 |
| WO | 2006/080024 | * 8/2006 |

OTHER PUBLICATIONS

What is Proteomics, Mar. 15, 2000.
www.cartesian.com—Nanoliter Quantitative Aspiration and Dispense (nQUAD) Technology, Mar. 15, 2000.
www.cartesiantech.com—Products for DNA Microarray Applications, Mar. 15, 2000.
www.cartesiantech.com—Synchronized nQUAD Technology, Mar. 15, 2000.
www.mbt.washington.edu—Leroy Hood, Research Focus, Mar. 15, 2000.
Medical Diagnosis Reagents, vol. 16.
Merriam-Webster's Collegiate Dictionary, 2001, Merriam-Webster Incorporated. 10th ed, 103.
Bruil, "In Vitro Leucocyte Adhesion to Modified Polyurethane Surfaces", Biomaterials, 1992 vol. 13, No. 13.
U.S. Appl. No. 10/213,345, filed Aug. 7, 2002, Glukhovsky et al.
U.S. Appl. No. 10/493,751, filed Apr. 27, 2004, Glukhovsky et al.
"The Heidelburg pH Capsule System Telemetric Fasting Gastric Analysis", Heidelburg International. Incorporated.
Heidelberger Kapsel—ein Kleinstsender fur die pH-Messung im Magen, Lange, et al., Telefunken-Zeitung, Jg 36 (1963) Heft 5, pp. 265-270.
"New Smart Plastic has Good Memory"—Turke, European Medical Device Manufacturer, devicelink.com.
"Robots for the Future"—Shin-ichi, et al. http://jin.jcic.or.jp/nipponaia13/sp05 html. printed Nov. 29, 2001.
"The Radio Pill", Rowlands, et al., British Communications and Electronics, Aug. 1960, pp. 598-601.
Video Camera to "TAKE"—RF System Lab, Dec. 25, 2001.
"Wellesley Company Sends Body Montiors into Space"—Crum, Boston Business Journal, 1998.
www.rfnorkia.com—NORIKA3, printed on Jan. 1, 2002.
"Wireless Transmission of a Color Television Moving Image from the Stomach using a Miniature CCD Camera, Light Source and Microwave Transmitter." Swain CP, Gong F, Mills TN. Gastrointest Endosc 1997;45:AB40, vol. 45, No. 4, 1997.
"In Pursuit of the Ultimate Lamp", Craford et al., Scientific American, Feb. 2001. pp. 49-53.
Manual of Photogrammetry, Thompson (Ed.), Third Edition, vol. Two,Copyright 1944, 1952, 1966 by the American Society of Photogrammetry.
www.jason.net/tinycam.htm, © 2001, printed Dec. 19, 2001.
www.middleeasthealthmag.com/article2.htm—Review proves the value of computers, © 2001, printed Nov. 29, 2001.
www.pedinc.com Personal electronic devices, © 1997.
BBC News Online—Pill camera to 'broadcast from the gut', Feb. 21, 2000, www.news.bbc.co.uk, printed Oct. 22, 2002.
"Transit times for the Capsule Endoscope", Gastrointestinal Endoscopy Apr. 2001; vol. 53:AB122.
W. Weitschies, R. Kotitz, D. Cordin, L. Trahms, "High-Resolution Monitoring of the Gastrointestinal Transit of a Magnetically Marked Capsule", (1997), Journal of Pharmaceutical Sciences, vol. 86, No. 11, pp. 1218-1222.

* cited by examiner

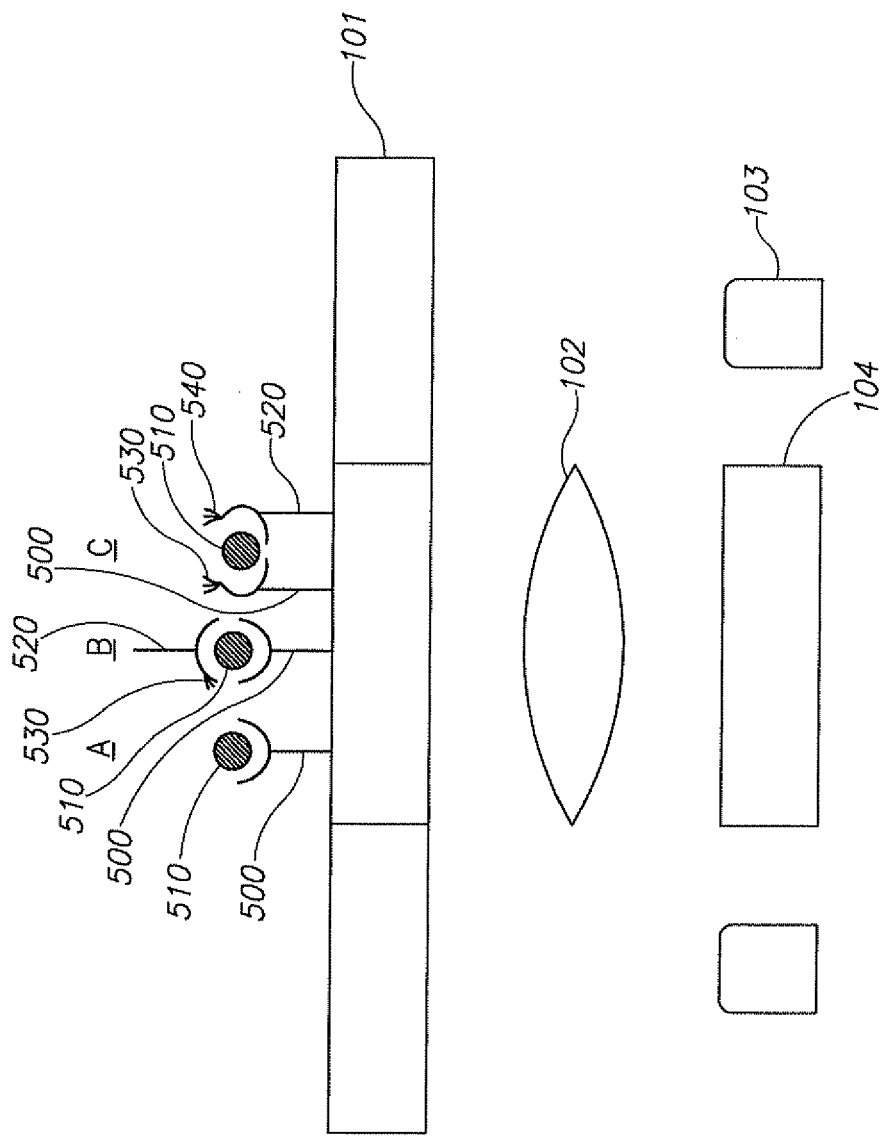

DEVICE AND METHOD FOR DETECTING IN-VIVO PATHOLOGY

CROSS REFERENCE TO RELATED APPLICATIONS

This application claims benefit from U.S. Provisional Patent Application No. 61/061,746, filed Jun. 16, 2008, U.S. Provisional Patent Application No. 61/090,123, filed Aug. 19, 2008, and U.S. Provisional Patent Application No. 61/159,260, filed Mar. 11, 2009, each of which is hereby incorporated by reference.

FIELD OF THE INVENTION

The present invention relates to the field of detecting in-vivo pathology. More specifically the present invention relates to a device and method for detecting in-vivo markers indicating pathology.

BACKGROUND OF THE INVENTION

The mammalian and human bodies enclose specific biological markers in-vivo, which may indicate various pathologies in the living body. Early detection of such markers could mean early detection of pathologies in the body, which would lead to better treatment. Each specific in-vivo marker can bind to a specific biological particle such as an antibody, peptide and other binding agents.

These markers may be detected by sensing an optical change which occurs due to binding of a binding agent to a marker in-vivo, for example, detecting fluorescence at a given bandwidth, emitted from a binding agent bound to a marker in-vivo.

An additional method of detecting binding between molecules is "Fluorescence resonance energy transfer" (FRET). In FRET, a molecule in its excited state can transfer energy to a second molecule proximate to it, to excite the second molecule as well. The distance between the molecules should typically be below 10 nm, so as to ensure the occurrence of the FRET procedure. One common configuration comprises one molecule attached to a solid phase while the other molecule may be in suspension. For example, the molecules may be two binding agents, one suspended in a fluid and one attached onto a solid phase in contact with the fluid. When both binding agents bind to an in vivo marker, they become sufficiently close to one another so as to undergo a FRET process. The optical change which may be detected in FRET is an emission of fluorescence from the binding agent excited second.

However, it may be difficult to sense an optical change of the same sort as described above when the quantity or concentration of an in-vivo marker is not high. It may also be difficult to detect specific bindings within an in-vivo environment, due to high background noise in this environment, i.e., reflected illumination other than the optical change to be detected.

There is, therefore, a need for an in-vivo sensing device which will have the ability to sense signals from in-vivo markers indicating pathology at a high signal to noise ratio.

Other methods of detecting markers include inhibiting fluorescence of a probe, and then, under certain conditions, such as conformational change or cleavage following marker attachment to the probe, activating it. One such method used for detection of nucleic acid markers is by using molecular beacons. Molecular beacons are single-stranded oligonucleotide hybridization probes that form a loop structure. The loop contains a sequence complementary to a target sequence, which is part of the marker being detected. At one end of the loop is attached a fluorophore and at the other end is a quencher. The loop conformation of molecular beacons causes the fluorophore and the quencher to be in high proximity to each other such that no fluorescence is exhibited. However, when molecular beacons hybridize to a nucleic acid strand containing a target sequence they undergo a conformational change that enables exhibition of fluorescence. The fluorophore that is no longer proximate to the quencher can now exhibit fluorescence.

Another method is by using a probe comprising more than one fluorophore attached to a backbone, wherein the fluorophores are positioned in great proximity to one another. The backbone may be a substrate to a marker being detected, which may be an enzyme. If a marker is present, the enzymatic marker cleaves the substrate. Following enzymatic cleavage the fluorophores draw away from one another and may exhibit fluorescence.

The methods mentioned above for detecting markers are efficient when the tests are being done in-vitro, in the case of molecular beacons, or when done in-vivo when the markers are intracellular and the probes detect them within the cells. However, there is a need for an in-vivo probe detecting presence of markers which are excreted from the cells.

SUMMARY OF THE INVENTION

Embodiments of the present invention provide a device and method for detecting in-vivo markers. Embodiments of the present invention provide a device which allows for free flow of in-vivo fluids through the device body.

According to some embodiments of the present invention, the device comprises a reacting layer onto which a binding agent is attached. The binding agent is typically a particle known to bind to a desired in-vivo marker. A continuous flow of in-vivo fluids through the device allows a long exposure time and raises the chance of successful binding of an in vivo marker to the binding agent which is attached onto the device.

According to some embodiments, an in-vivo sensing device for detecting in-vivo pathology is provided. The in-vivo device may comprise a device body comprising an opaque cover or a reference background. The reference background may be positioned at an end of the device body, but may also be positioned in other location along the device body. In some embodiments, the device body may enclose a reacting layer having at least one type of binding agent attached thereon. The reacting layer may be positioned at the end of the device body, perpendicular to a forward sensing direction. In other embodiments, the reacting layer may be positioned parallel to a forward sensing direction of the device. The device body may further enclose a sensor configured to sense an optical change on said reacting layer, and at least one illumination source configured to illuminate the reacting layer. In some embodiments, the sensor and illumination source may face the reacting layer such that rays from the illumination source impinge on the reacting layer, prior to impinging on the opaque cover, and are then emitted to the sensor.

In some embodiments, the opaque cover comprises at least two openings to allow flow of in vivo fluids through the device body.

In some embodiments, the optical change detected by the sensor is selected from a group consisting of: a change of color, a change of hue, a change of brightness or intensity, a change of optical density, a change of transparency, a change of light scattering or any combination thereof.

In some embodiments, the at least one illumination source comprises a white LED. In some embodiments, the illumination source comprises a monochromatic illumination source. In other embodiments, the device may comprise more than one illumination source, wherein each of the illumination sources has a different illumination spectrum.

In some embodiments, the reacting layer may include a substance, selected from a group consisting of: silicon, glass, and plastic.

In some embodiments, the openings in the opaque cover are shaped so as to induce continuous flow of fluids in and out of the device body. In some embodiments, the opaque cover comprises a mirror.

In some embodiments of the invention, the sensor comprises an array of light sensitive elements having differing sensitivity spectra.

In some embodiments, the device is a swallowable capsule.

According to some embodiments, a method for detecting in-vivo pathology is provided. The method may comprise the steps of: administering an in vivo sensing device comprising a reacting layer and a background and contacting the reacting layer having at least one type of binding agent attached thereon, with a flow of endo-luminal content. The method may further comprise viewing the reacting layer upon the background to detect an optical change occurring due to binding of the binding agent to a marker in vivo. In some embodiments, the in-vivo marker is excreted from an in-vivo lumen into in-vivo fluids flowing inside a lumen.

In some embodiments, the method may comprise the step of administering to a patient a binding agent with a tag, wherein the tagged binding agent has an affinity for the marker. In some embodiments, the tag may be selected from the group of gold particles, beads, and fluorescence emitting molecule.

According to other embodiments, there is provided a method for detecting in-vivo pathology comprising the steps of: contacting a reacting layer having a first and second binding agent attached thereon, with endo-luminal content, wherein the first and second binding agents have attached thereon a first and second fluorescent molecule, respectively. The method may further comprise viewing the reacting layer upon a background to detect emitted fluorescence from the second fluorescent molecule.

According to some embodiments, the reacting layer is included in a swallowable capsule.

In some embodiments, another in-vivo sensing device for detecting in-vivo pathology is provided. The in-vivo device may enclose a reacting layer which may include a binding agent, a fluorophore attached to the binding agent, and a quencher attached to the binding agent. The device may further comprise a sensor configured to sense an optical change on the reacting layer, and at least one illumination source configured to illuminate the reacting layer. In some embodiments, the sensor and illumination source may face the reacting layer such that rays from the illumination source impinge on the reacting layer and may then be emitted to the sensor. In some embodiments, the device body may include at least two openings to allow in vivo fluids to flow through the device body and over the reacting layer. In some embodiments, the quencher attached to the binding agent may be drawn apart from the fluorophore when an in-vivo marker flowing in in-vivo fluids binds to the binding agent, to enable an optical change to occur.

According to some embodiments, an additional in-vivo sensing device for detecting in-vivo pathology is provided. The device may enclose a reacting layer which may comprise a binding agent attached thereon, and at least two fluorophores attached to the binding agent in high proximity to each other to inhibit fluorescence emission. In some embodiments, the device may further include a sensor configured to sense an optical change on said reacting layer, and at least one illumination source configured to illuminate the reacting layer. In some embodiments, the sensor and illumination source may face the reacting layer such that rays from the illumination source impinge on the reacting layer and are then reflected to the sensor. In some embodiments, the device body may include at least two openings to allow in vivo fluids to flow through the device body and over the reacting layer. In some embodiments, the at least two fluorophores are drawn apart when an in vivo marker binds to the binding agent, to enable an optical change to occur.

According to some embodiments, another in-vivo sensing device for detecting in-vivo pathology is provided. The in-vivo device's body may enclose a reacting layer including a noble metal film, and a binding agent attached to the noble metal film. In some embodiments, the device may include a sensor configured to detect an angle shift of illumination emitted from the reacting layer due to binding of an in-vivo marker to the binding agent. In some embodiments, the device may include at least one illumination source configured to illuminate the reacting layer at a predetermined angle. In some embodiments, the sensor and illumination source may face the reacting layer such that rays from the illumination source impinge on the reacting layer and are then reflected to the sensor. In some embodiments, the device body may include at least two openings to allow in vivo fluids to flow through the device body and over the reacting layer. In some embodiments, the sensor may be a vector detector.

BRIEF DESCRIPTION OF THE DRAWINGS

The present invention will be understood and appreciated more fully from the following detailed description taken in conjunction with the appended drawings in which:

FIG. 5A is a schematic illustration of a reacting layer included in an in-vivo sensing device in accordance with another embodiment of the invention;

Figure 1:
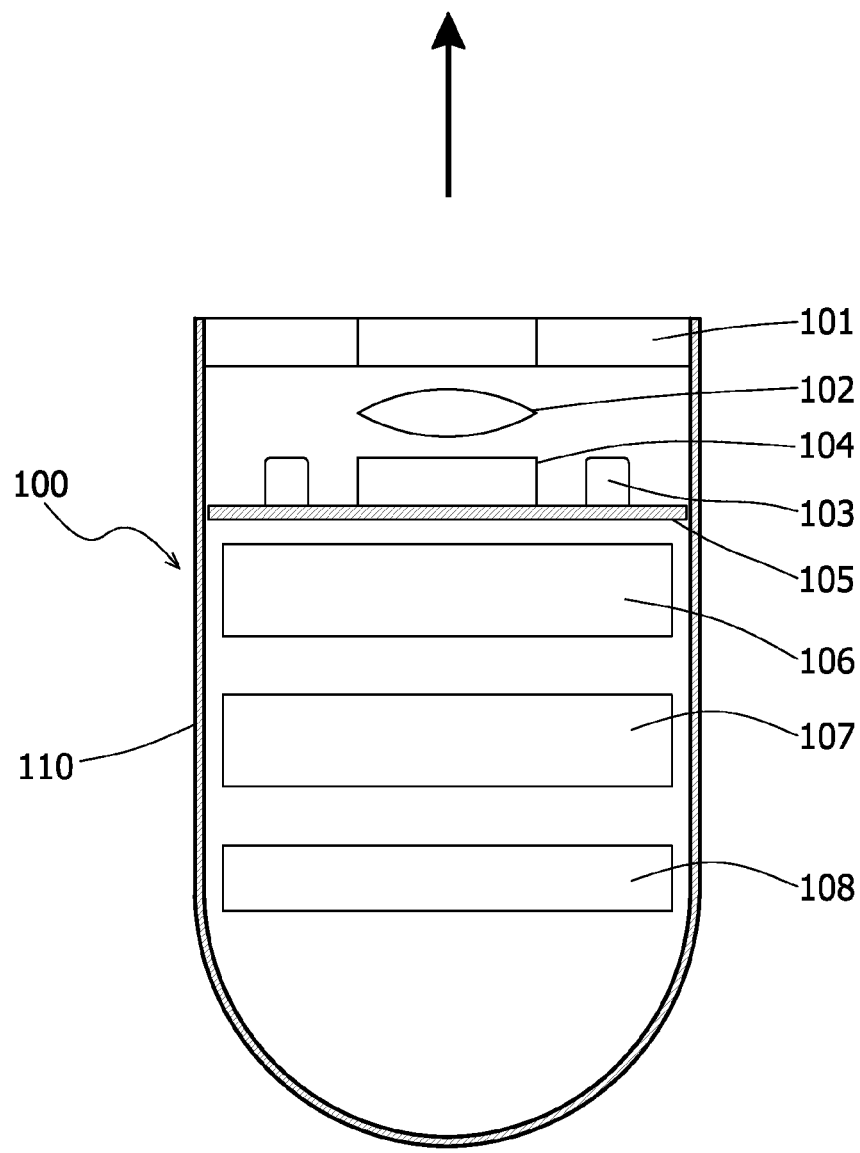
FIG. 1 is a schematic illustration of an in-vivo sensing device in accordance with one embodiment of the invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as to not obscure the present invention.

Reference is now made to FIG. 1, which provides a schematic illustration of an in-vivo sensing device in accordance with one embodiment of the invention. According to one embodiment, the in vivo sensing device is a swallowable imaging capsule. According to an embodiment of the invention, as described in FIG. 1, there is provided an in-vivo sensing device 100, comprising a reacting layer 101, which is positioned at the end of the device body 110. Reacting layer 101 may be perpendicular to a forward sensing direction of device 100. However, in other embodiments, reacting layer 101 may be located in other positions along device body 110, e.g. reacting layer 101 may be parallel to a forward sensing direction of device 100. Reacting layer 101 may have attached thereon at least one type of binding agents or capturing agents, e.g. antibodies or other suitable peptides, proteins, glycoproteins, specific carbohydrates, specific DNA or RNA fragments. The binding/capturing agent is typically specific to or has a high affinity to a desired in-vivo marker.

In-vivo sensing device 100 is exposed to the in-vivo surroundings. Reacting layer 101 is exposed to in-vivo fluids flow, with or without prior mechanical pre-filtering of large particles and unwanted aggregates, and is so exposed to in-vivo markers flowing within the in-vivo fluids. This constant exposure may aid in achieving binding of a desired in-vivo marker to the binding/capturing agent at high concentrations of the in-vivo marker. A higher concentration of in-vivo markers may have a better chance to bind to the binding agent attached onto reacting layer 101.

According to other embodiments, a tagged binding agent may be administered to the patient. The tagged binding agent is typically specific to or has a high affinity to the desired in-vivo marker, but typically directed to a different site on the marker structure than the site where the binding/capturing agent is bound. When the in vivo marker is bound to the binding agent, they are both immobilized to reacting layer 101. The binding agent with the tag may then bind to the immobilized marker and then may be detected by sensor 104. Optical system 102 may be designed so it is focused on reacting layer 101 and does not focus illumination reflected from the surroundings onto sensor 104, and so illumination from the background will not be substantially detected by sensor 104. Thus, if the tagged binding agent does not bind to the marker, it will not be seen by sensor 104 since it will continue to flow with the in-vivo fluids surrounding it. Detection of the tag will typically indicate that the marker is bound to the binding agent and so may indicate pathology. The tagged binding agent may be inserted into the body through drinking, injection or any other suitable method. Typically the insertion of the tagged binding agent may occur after a preset time period following insertion of the in vivo sensing device, such as device 300 or device 400.

The binding agent may be tagged with gold particles or beads which may be detectable when illuminated in visible light wavelengths or in near Infrared (near IR) wavelengths. In other embodiments, the binding agent may be tagged with a fluorescent molecule or a nano-container carrying a large quantity of fluorescent molecules. When the sensor, such as sensor 104 or image sensor 404, detects the presence of the gold particles, beads or fluorescent tagging molecules, it can be inferred that the desired in vivo marker is bound to the binding agent.

If an optical change occurring due do binding of an in-vivo marker to the binding agent is viewed, then there is an indication of the presence of an in-vivo marker sought, which presence indicates pathology present in-vivo.

According to some embodiments, a sensor 104 is positioned with a view of the reacting layer 101, so that an optical change occurring on the reacting layer 101 may be detected by the sensor 104. The optical change may be a change of color, a change of hue, a change of brightness or intensity, a change of optical density, a change of transparency, a change of light scattering or any combination thereof.

The optical change occurring on reacting layer 101 and sensed by sensor 104 is one which may occur due to a structural change in either the binding agent or the in-vivo marker bound to it, or in both. As shown in FIG. 5A at area A, where binding agent 500 is attached onto reacting layer 101, in-vivo marker 510 binds to binding agent 500. The binding between binding agent 500 and in-vivo marker 510 may cause a structural change in either binding agent 500, or in in-vivo marker 510 or in both, which may lead to an optical change.

According to some embodiments, reacting layer 101 may be fabricated from various materials that are suitable for immunoassay, e.g. silicon, glass, plastic etc. Parameters to be considered while assessing if a material is suitable for manufacturing reacting layer 101, may be, for example, the material's transparency, its safety for internal use, its durability under endo-luminal conditions and so on. Therefore, any material known in the art for manufacture of a biological layer for attaching a binding agent thereon may be suitable. According to some embodiments, reacting layer 101 may be a transparent lab-on chip type layer, which would allow various reactions to take place on it and to be sensed by sensor

104. According to other embodiments, composites such as polystyrene are also suitable for constructing reacting layer 101.

In some embodiments, there may be provided an optical system 102 which may typically comprise a lens. The lens focuses the optical change onto sensor 104. Optical change may be, for example, the illumination emitted from the binding agent attached onto reacting layer 101. In some embodiments, optical system 102 is designed for only focusing illumination emitted from a predetermined distance, which may be the distance between optical system 102 and reacting layer 101. When optical system 102 is designed as such, illumination emitted from farther distances would not be focused onto sensor 104 and would not be sensed by it, and so background "noise", e.g., sensing of illumination other than the optical change, is substantially avoided.

In some embodiments, there is provided at least one illumination source 103. According to some embodiments, sensor 104 and illumination source 103 may face said reacting layer 101 such that rays from the illumination source 103 impinge on the reacting layer 101, and are then emitted onto the sensor 104. According to some embodiments, the area of reacting layer 101 onto which the binding agents are attached is of a size correlating to the size of sensor 104, so that the information from reacting layer 101 would be detected in its entirely by sensor 104 without any missed data.

Typically, illumination source 103 is a white LED. According to other embodiments, illumination source 103 may be a monochromatic illumination source or an illumination source having a specified illumination spectrum. In some embodiments, there may be more than one monochromatic illumination source. According to other embodiments, there may be more than one illumination source 103 while each of the illumination sources may have a different illumination spectrum.

According to some embodiments, each illumination source 103 having a different spectra may illuminate either the same type of binding agents attached onto reacting layer 101 or may illuminate more than one type of binding agent attached. When illuminating with more than one illumination source 103 each having different spectra of illumination, sensor 104 may receive various reflections at different illumination spectra. In some embodiments, the variety of reflections may provide additional information on pathology that might be present in the living body. The sensed optical change occurring due to binding of in-vivo markers to binding agents, in the first scenario (one type of binding agents) may provide information on one type of pathology and in the second scenario (more than one type of binding agent) may provide information on various types of pathologies, when each in-vivo marker binds to a different binding agent.

According to other embodiments, there may be one monochromatic illumination source 103 (e.g., an LED) illuminating various types of binding agents. This embodiment may assist in detecting more than one type of pathology simultaneously. According to some embodiments, sensor 104 may comprise an array of light sensitive elements having differing sensitivity spectra. So, that if device 100 comprises more than one illumination source 103 and each illuminates at a different predetermined band width, sensor 104 may sense the different reflected illuminations. In some embodiments, sensor 104 may comprise an array of different fluorescent filters which allow transmittance of specific wavelengths.

In some embodiments, in order to detect the presence of an in vivo marker indicating pathology, there may be a need to initiate binding of a tagged binding agent to the marker. According to some embodiments, following binding of the in vivo marker to the binding agent, which is attached onto reacting layer 101, an additional binding agent, for example an antibody, may be inserted into the body lumen. This inserted binding agent is typically specific to or has a high affinity to the desired in-vivo marker, typically to a different site on the marker structure, than the site where the binding agent attached on reacting layer 101 is bound. The inserted binding agent may be tagged, for example, with gold particles, beads or a tagging molecule which may exhibit fluorescence. According to some embodiments, the inserted binding agent may be tagged with a nano-container which may carry or comprise a large quantity, e.g. thousands, of fluorescent molecules. Since such beads may contain a large quantity of fluorescent molecules, these nano-containers may be useful for increasing the fluorescent signal, i.e., optical change. Examples of nano-containers may be polystyrene beads, liposomes and silica beads. Other nano-containers may be used. Therefore, in some embodiments, following binding of the in vivo marker to the binding agent attached to reacting layer 101, the tagged binding agent may bind to the marker at a different site, creating a complex of binding agent, marker and tagged binding agent. When reacting layer 101, onto which the complex is attached, is illuminated, sensor 104 may detect an optical change indicating the different bound molecules and, thus, the presence of pathology.

According to some embodiments, the binding agent inserted into the body lumen may be inserted by drinking, swallowing, injecting, etc. Typically the insertion of the binding agent would be done after a preset time period following insertion of device 100 into the body. In some embodiments, device 100 may be inserted into the body, and after a given time period, which may allow binding of the desired in vivo marker to the binding agent on reacting layer 101, the tagged binding agent would be inserted into the body.

According to some embodiments, the inserted binding agent may be tagged with gold particles, beads, a molecule exhibiting fluorescence, a nano-container carrying fluorescent molecules or any other tagging technique which may be noticeable when illuminated. When the binding agent is tagged with, for example, gold particles or beads, it may be noticed when illuminated in wavelengths of visible light. When, for example, the binding agent is tagged with a fluorescent emitting tagging molecule or a nano-container with fluorescent molecules, the binding agent may be noticeable when illuminated in spectra suitable for inducing fluorescence, e.g., illumination in an ultraviolet spectrum may cause emission in visible light spectrum. As shown in FIG. 5A at area B, binding agent 500 is attached on reacting layer 101, and in-vivo marker 510 binds to it. Binding agent 520 tagged with a tag 530 is administered into the lumen and then binds to the in-vivo marker 510, which is already immobilized on reacting layer 101. When reacting layer 101 is illuminated, tag 530 may be noticeable and detected by sensor 104.

According to some embodiments, there may be two binding agents attached onto reacting layer 101. Reacting layer 101 may act as a solid phase, and therefore there may be two binding agents attached onto one solid phase. Both binding agents are typically specific to or have a high affinity to a desired in-vivo marker, where typically, but not necessarily, each one of the binding agents has a high affinity to a different site on the in vivo marker structure. In some embodiments, each of the two binding agents is tagged with a tagging molecule which may exhibit fluorescence. When an in vivo marker binds to the two binding agents, the binding agents attached onto the reacting layer 101 solid phase become closer than they were prior to the binding of the in vivo marker. When the two binding agents are in the new closer position, the two tagging molecules are then in close proximity to one another, enough to enable "Fluorescence Resonance Energy Transfer" (FRET) when reacting layer 101 is illuminated. Typically, the distance between the tagging molecules should be between 1-10 nm, so as to enable FRET to occur. Illumination from illumination source 103 may excite one of the tagging molecules to transfer energy to the other tagging molecule, so that this second molecule is also excited and emits fluorescence. The fluorescence emitted by the second molecule may be detected by sensor 104, and thus indicate the presence of an in vivo marker.

As shown in FIG. 5A at area C two binding agents 500 and 520 are attached onto solid phase 101. Binding agent 500 is tagged with tagging molecule 530 and binding agent 520 is tagged with tagging molecule 540. When in-vivo marker 510 binds to both binding agents 500 and 520, they become closer and so tagging molecules 530 and 540 are in close proximity to one another enough to enable FRET. When reacting layer 101 is illuminated, tagging molecule 530, for example, may exhibit fluorescence and transfer energy to tagging molecule 540. Tagging molecule 540 may then be excited and emit fluorescence, which may be sensed by sensor 104.

Reacting layer 101 may be constantly viewed by sensor 104, and so a long exposure time may be achieved. This is an important feature especially when an optical change detected is fluorescence related. In fluorescence, the number of photons absorbed by the molecule illuminated is greater than the number of photons emitted from it. Therefore, in order to obtain a high signal, the preferable way is sensing a static image, such as sensing a reacting layer 101, which is constantly in contact with in vivo fluids, and is constantly viewed for optical changes.

The in vivo marker may be carried within the in vivo fluids which freely flow near device 100. In some embodiments, presence of the in vivo marker may be indicative of pathology originating in different parts of the body. The marker may be indicative of pathology in the gastrointestinal (GI) tract, through which device 100 may pass. Examples of in vivo markers according to embodiments of the invention include MUCIN-1 and EGFR, which are typically related to colorectal diseases, and MMP-7 and CEA, which are typically related to colorectal and gastric diseases. Pepsinogen I/II, Gastrin 17, Buforin, Cytokeratin 8-CK-8, AMP18/Gastrokine 1, CA19-9, CA 72-4, Reg IV, Phosphorylated form of histone H2A, and ApoE are examples of markers typically related to gastric diseases.

According to some embodiments, sensor 104 may comprise larger pixels than the size of pixels typically used for imagers, such as CCD or CMOS. For example, sensor 104 may comprise pixels of up to 100 microns.

According to some embodiments, at least one illumination source 103 and sensor 104 are placed on a PCB 105. Typically, device 100 may be autonomous and may comprise an internal power source 106, e.g., batteries. According to other embodiments, device 100 may be connected to an external power source through wires or cables.

According to some embodiments, device 100 may comprise a transmitter 107 to transmit the data sensed by sensor 104 to a receiver external to the device 100. In some embodiments, transmitter 107 may include a wireless transmitter, e.g., able to transmit Radio Frequency (RF) signals, or able to transmit other types of communication signals. For example, transmitter 107 may transmit wireless signals utilizing an antenna 108. Other wireless methods of transmission may be used.

A system, according to some embodiments of the invention, may include an in-vivo sensing device 100, transmitting information (e.g., images and/or other data) to a data receiver and/or recorder possibly close to or worn on a subject. A data receiver and/or recorder may of course take other suitable configurations. The data receiver and/or recorder may transfer the received information to a larger computing device, such as a workstation or personal computer, where the data may be further analyzed, stored, and/or displayed to a user. In other embodiments, each of the various components need not be required and or may be housed in alternate configurations; for example, an internal device may transmit or otherwise transfer (e.g., by wire) information directly to a viewing or processing system. In another example, the data receiver or workstation may transmit or otherwise transfer information to the in-vivo device. While in one embodiment the device may be an autonomous capsule, other configurations, such as an endoscope or trocar, may be used.

It is noted that some embodiments of the present invention may be directed to an autonomous, typically ingestible in-vivo device. Other embodiments need not be ingestible. A receiving and/or display system suitable for use with embodiments of the present invention may be similar to embodiments described in U.S. Pat. No. 7,009,634 and/or in U.S. Pat. No. 5,604,531. Devices and systems as described herein may have other configurations and other sets of components.

Figure 2:
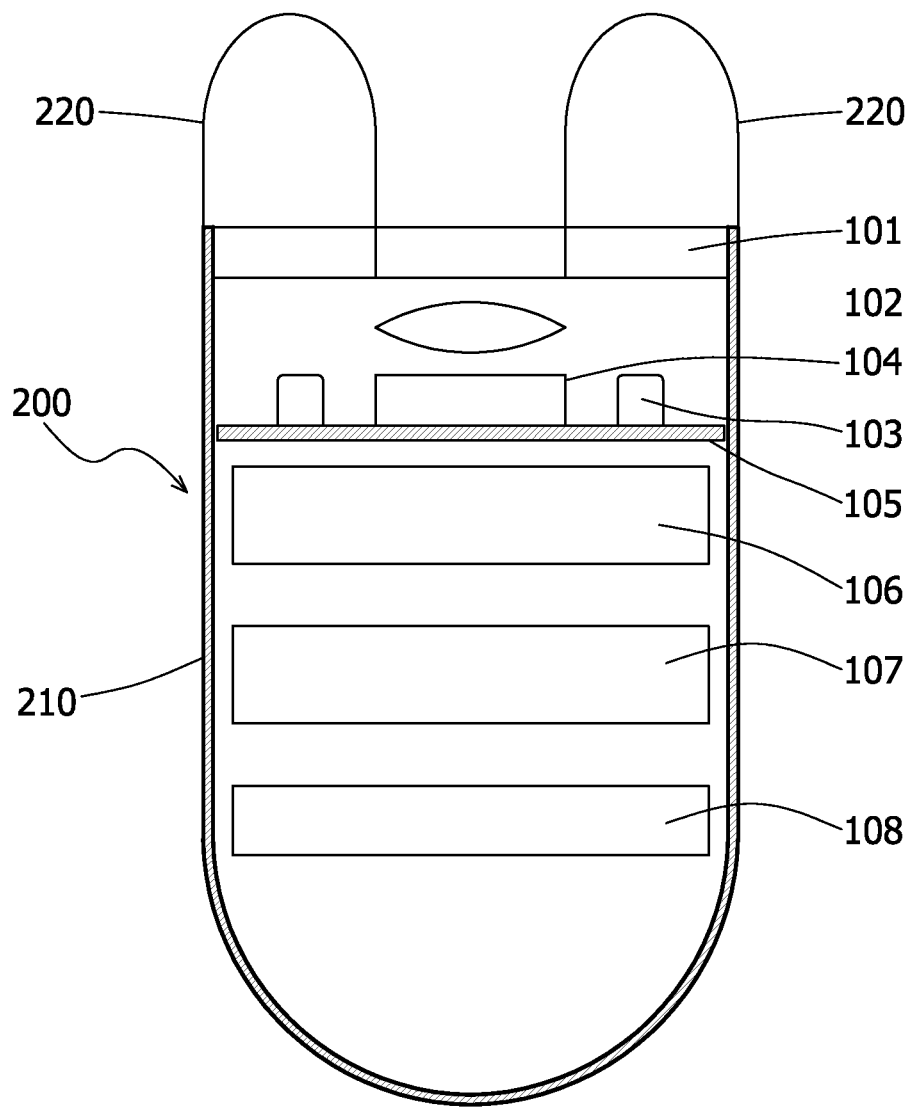
FIG. 2 is a schematic illustration of an in-vivo sensing device in accordance with another embodiment of the invention.

Reference is now made to FIG. 2, which provides a schematic illustration of an in-vivo sensing device in accordance with another embodiment of the invention. According to embodiments of the invention as shown in FIG. 2, there is provided an in-vivo device 200 which is similar to device 100 but with the addition of at least two protrusions 220 on top of or covering reacting layer 101. The protrusions 220 may push the lumen wall or other tissue away from reacting layer 101. When reacting layer 101 is proximate to the lumen wall, illumination from illumination source 103 may reach the lumen wall as well as reacting layer 101. The illumination may cause an optical change in the lumen wall or tissue proximate to reacting layer 101, which may be detected by sensor 104. For example, illumination from illumination source 103 may lead to emission of auto-fluorescence from the lumen wall or tissue, which may interfere with the illumination emitted from reacting layer 101. In order to avoid such background noise and achieve a high signal to noise ratio in the sensed data, protrusions 220 may push the lumen wall or in vivo tissue away from reacting layer 101. However, in some embodiments, reacting layer 101 is kept exposed at the area where the binding agents are positioned, so protrusions 220 may still enable contact between reacting layer 101 and in vivo fluids, to enable binding of in vivo markers flowing in the fluids.

Figure 3:
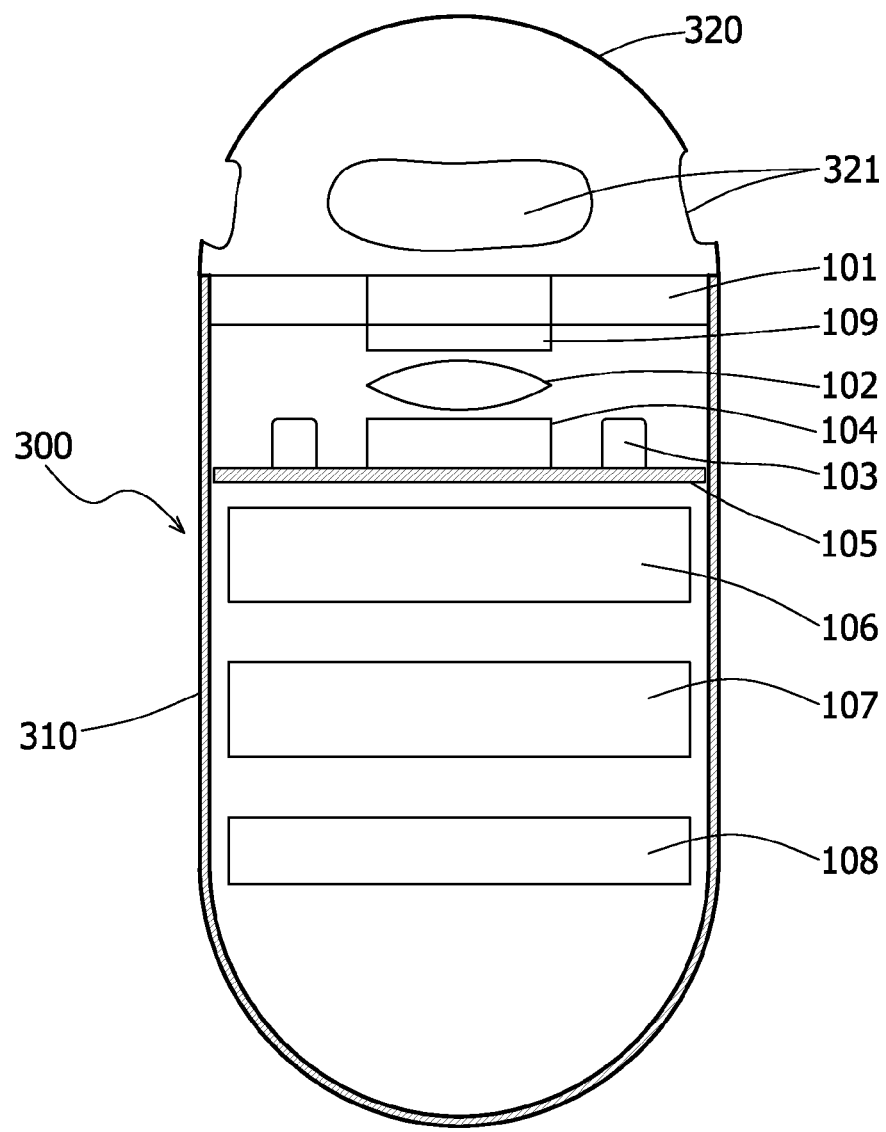
FIG. 3 is a schematic illustration of an in-vivo sensing device in accordance with yet another embodiment of the invention.

Reference is now made to FIG. 3, which provides a schematic illustration of an in-vivo sensing device in accordance with yet another embodiment of the invention. According to embodiments of the invention as described in FIG. 3, there is provided an in-vivo sensing device similar to device 100, but with an addition of an opaque cover (or reference background) 320 attached at the end of a device body 310, in front of reacting layer 101, perpendicular to a forward sensing direction. Opaque cover 320 pushes the lumen wall away from reacting layer 101 and in addition provides better isolation for reacting layer 101 from the in vivo surroundings. In other embodiments, opaque cover 320 and reacting layer 101 may be positioned at a different location along the device body 310, e.g., opaque cover 320 and reacting layer 101 may be positioned parallel to a forward sensing direction of device 300, while opaque cover 320 is always positioned in front of reacting layer 101.

Opaque cover 320 assists in isolating data sensed in device 300 from data which may be sensed from the surroundings without the presence of opaque cover 320. By having an opaque cover 320 rather than a transparent one (for example as is known in swallowable imaging capsules), device 300 has the ability of sensing and collecting information of reactions occurring within device 300 alone, without any interference from reactions occurring externally to device 300. This assists in achieving a high signal to noise ratio in the sensed data.

In some embodiments, opaque cover or reference background 320 may provide reference to reactions occurring within device 300, i.e., indication as to whether the data acquired by sensor 104 indicates pathology or whether it is data acquired from particles flowing through device 300 but not attached to it. Comparing data acquired by sensor 104 of reacting layer 101 with to data acquired by sensor 104 of reacting layer 101 without a reaction enables a determination of whether the data detected by the sensor 104 indicates specific binding between the binding agents and the marker or whether it is merely signals emitted from the in-vivo fluids flowing in proximity to the reacting layer 101. For example, since freely flowing in-vivo fluids may comprise fluorescently tagged binding agents (e.g., tagged binding agents 520 shown in FIG. 5A at area B) that are not bound to reacting layer 101, fluorescence may be detected from the "background", i.e., the in-vivo fluids, and not only from reacting layer 101.

The opaque cover 320 comprises at least two openings 321 to allow continuous flow of in-vivo fluids through device body 310. According to some embodiments, the shape of openings 321 may be one that induces the flow of in-vivo fluids through them, e.g., the shape of a nostril or trapezoid, which has a large diameter at the interface of the opening 321 and the in-vivo fluids and a decrease in diameter along the thickness of cover 320. This could increase the concentration of fluids passing through device 300 and so increase the quantity of in-vivo markers carried within the in vivo fluids which freely flow through the at least two openings 321 into the space created within opaque cover 320.

According to some embodiments, a mirror may replace opaque cover 320. In addition, reacting layer 101 may comprise a semi transparent mirror 109. This semi transparent mirror may be positioned beneath reacting layer 101 and above optical system 102. The semi transparent mirror 109 may act as a mirror for reflecting illumination at certain wavelengths and yet enabling some percentage of rays to pass through it and onto sensor 104, while not acting as a barrier or reflectance to other wavelengths.

Illumination source 103 provides illumination rays at a certain wavelength, onto reacting layer 101, through the semi transparent mirror 109 positioned between illumination source 103 and layer 101. Some of the rays may be absorbed by the binding agents attached onto the reacting layer 101, some may be reflected from reacting layer 101, and some may pass through the reacting layer 101. In this embodiment, the rays which pass through the reacting layer 101 may reach the mirror replacing opaque cover 320. The illumination rays reaching the mirror may be reflected by the mirror towards sensor 104. The semi transparent mirror 109 may enable passage through it and onto sensor 104 of some percentage of the rays reflected from the mirror, while some percentage of those rays would be reflected by the semi transparent mirror 109 back onto reacting layer 101, and vice versa. In this embodiment, data with a high signal to noise ratio may be acquired. Since illumination rays are reflected onto reacting layer 101 more than once, the percentage of rays absorbed by reacting layer 101 by the binding agents and the in vivo markers bound to them, is increased, which may also increase the percentage of illumination detected by sensor 104.

According to some embodiments, device 300 may be a swallowable capsule. According to other embodiments, device 300 may be of a capsule shape or of any other shape such as a sphere, an ellipsoid, a peanut, etc. In other embodiments, opaque cover 320 need not be of a dome shape, as shown in FIG. 3, but rather may be, for example, flat.

Figure 4:
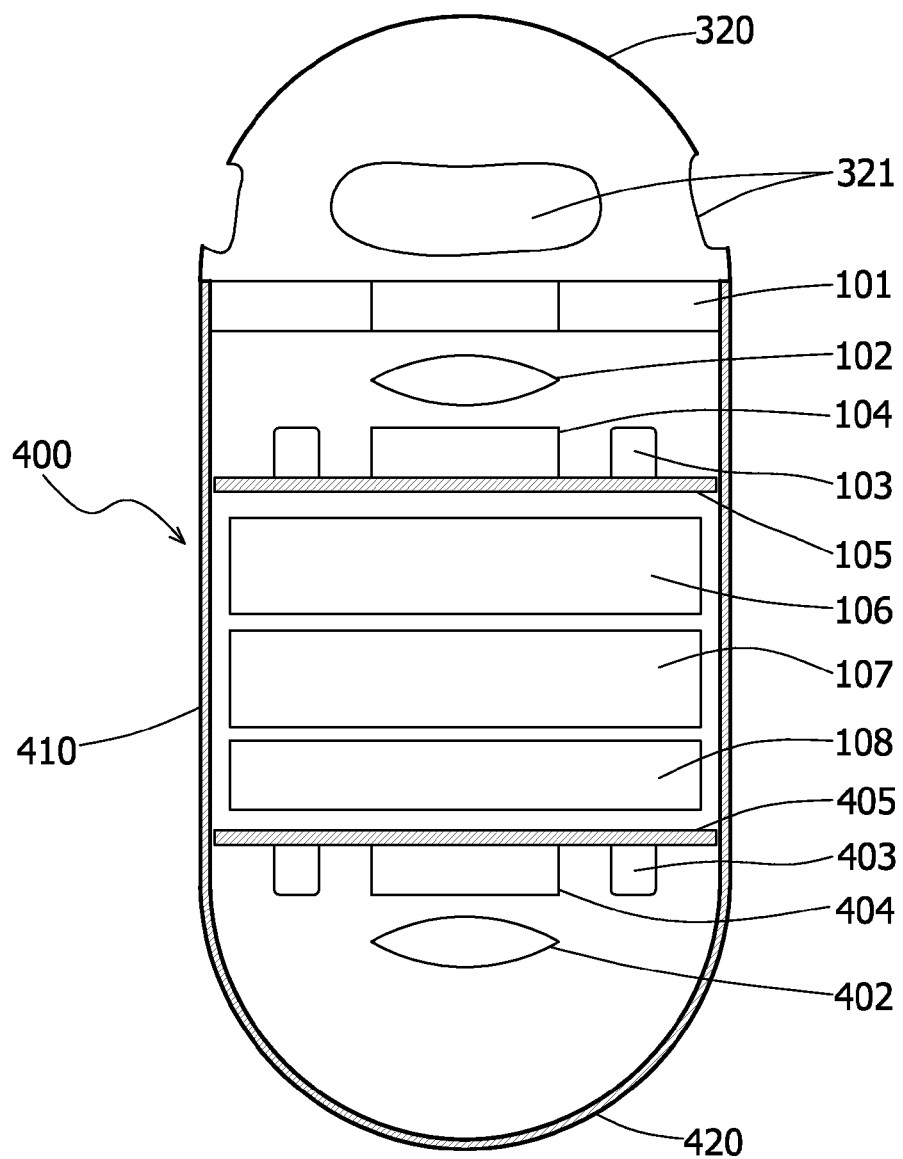
FIG. 4 is a schematic illustration of an in-vivo sensing device in accordance with another embodiment of the invention.

Reference is now made to FIG. 4, which provides a schematic illustration of an in-vivo sensing device in accordance with another embodiment of the invention. According to embodiments of the invention as shown in FIG. 4, there is provided an in-vivo device 400 which is similar to device 300 but with the addition of another sensing head 420. According to some embodiments, an image sensor 404 is positioned at an end of device body 410, opposite the end of sensor 104, behind dome 420.

Image sensor 404 may be used for imaging the lumen into which device 400 is inserted. In some embodiments, imager 404 may be a CCD or CMOS imager, with pixel size of, for example, 5-6 microns. According to some embodiments, imager 404 may acquire images of the body lumen, whereas sensor 104 senses an optical change due to binding of in-vivo marker to a binding agent. Therefore, data of the location in a lumen, at which pathology is present, may be acquired using image sensor 404.

According to some embodiments, imager 404 may acquire images simultaneously with image acquisition by sensor 104, or may acquire images consecutively with image acquisition by sensor 104. According to some embodiments, imager 404 may be controlled by a user, e.g., a physician. For example, a physician may receive sensed data from sensor 104 in real-time and, when an optical change is sensed, the physician may activate imager 404 to acquire images of the lumen at the location of the optical change. In some embodiments, a physician may activate sensor 104 according to an image acquired by image sensor 404, which seems to indicate pathology.

According to other embodiments, imager 404 and/or sensor 104 may be activated automatically in response to an image or other optical data sensed by either of the sensors (sensor 104 or imager 404). Image analysis or other recognition algorithms may be used in this embodiment. An image may be analyzed on board the device or in an external device (such as in a receiver) and a command may be sent to the required sensor (sensor 104 or imager 404) based on the analysis.

According to some embodiments, there may be provided at least one illumination source 403, to illuminate a lumen into which device 400 is inserted. In some embodiments, in front of image sensor 404 there may be provided an optical system 402 to focus illumination emitted from the lumen onto imager 404 for image acquisition.

According to some embodiments, device 400 may be autonomous and may comprise an internal power supply 106, e.g., a battery. Device 400 may comprise more than one battery 106, or may be externally powered, for example by power induction to the battery or through wires or cables to an external power source.

In some embodiments, device 400 may comprise a transmitter 107. Transmitter 107 may transmit either data sensed by sensor 104 or image data acquired by imager 404, or both. In some embodiments, device 400 may comprise more than one transmitter for transmitting data acquired by device 400. There may be one transmitter for transmitting data sensed by sensor 104 and one for transmitting image data acquired by imager 404. According to some embodiments, transmitted data may be transmitted to an external receiver (not shown). The external receiver may receive data simultaneously from the at least two transmitters.

According to some embodiments, device 400 may be a swallowable capsule. According to other embodiments, device 400 may be a capsule shape or of any other shape such as a sphere, an ellipsoid, a peanut etc.

According to some embodiments, it may be possible to determine pathology by measuring a ratio between the detected presence of in-vivo markers. In some embodiments, the predictor for pathology may be the ratio of the detected presence of one marker vs. that of another marker rather than, or in addition to, the concentration of either one of the markers alone. For example, the ratio between the presence of Pepsinogen I and the presence of Pepsinogen II, which is known as "serum pepsinogen test", may indicate the presence of gastric cancer. According to some embodiments, there may be a binding agent attached onto reacting layer 101, which may have a high affinity to the two in-vivo markers whose ratio is sought. Each in-vivo marker may be specific or with high affinity to the binding agent structure. Following the insertion of device 100 into the body, a free flow of in-vivo fluids is in contact with reacting layer 101, so that the in-vivo markers desired may bind to the binding agent. Since free and continuous flow of in vivo fluids is made possible near reacting layer 101, it can be inferred that the ratio between the markers bound to the binding agent is the same as the ratio between the in vivo markers flowing in the in vivo fluids.

In some embodiments, there may be inserted into the body two different binding agents, each specific or with high affinity to a different marker. These inserted binding agents may have attached thereon a tagging molecule, which may for example exhibit fluorescence when illuminated. After the tagged binding agents are inserted into the body, for example by the patient drinking them, they may bind to their appropriate marker. (see FIG. 5A at area B Illumination source 103 may illuminate reacting layer 101 and so the tags of the binding agents may exhibit fluorescence which may be detected by sensor 104. In order to distinguish between the two in vivo markers, the tagging molecules may be chosen such that they emit illumination at different wavelengths. The sensor 104 may comprise an array of different fluorescent filters to detect the different illumination spectra emitted from the tagging molecules, and the ratio between the different spectra may indicate the ratio between the in vivo markers.

Figure 5B:
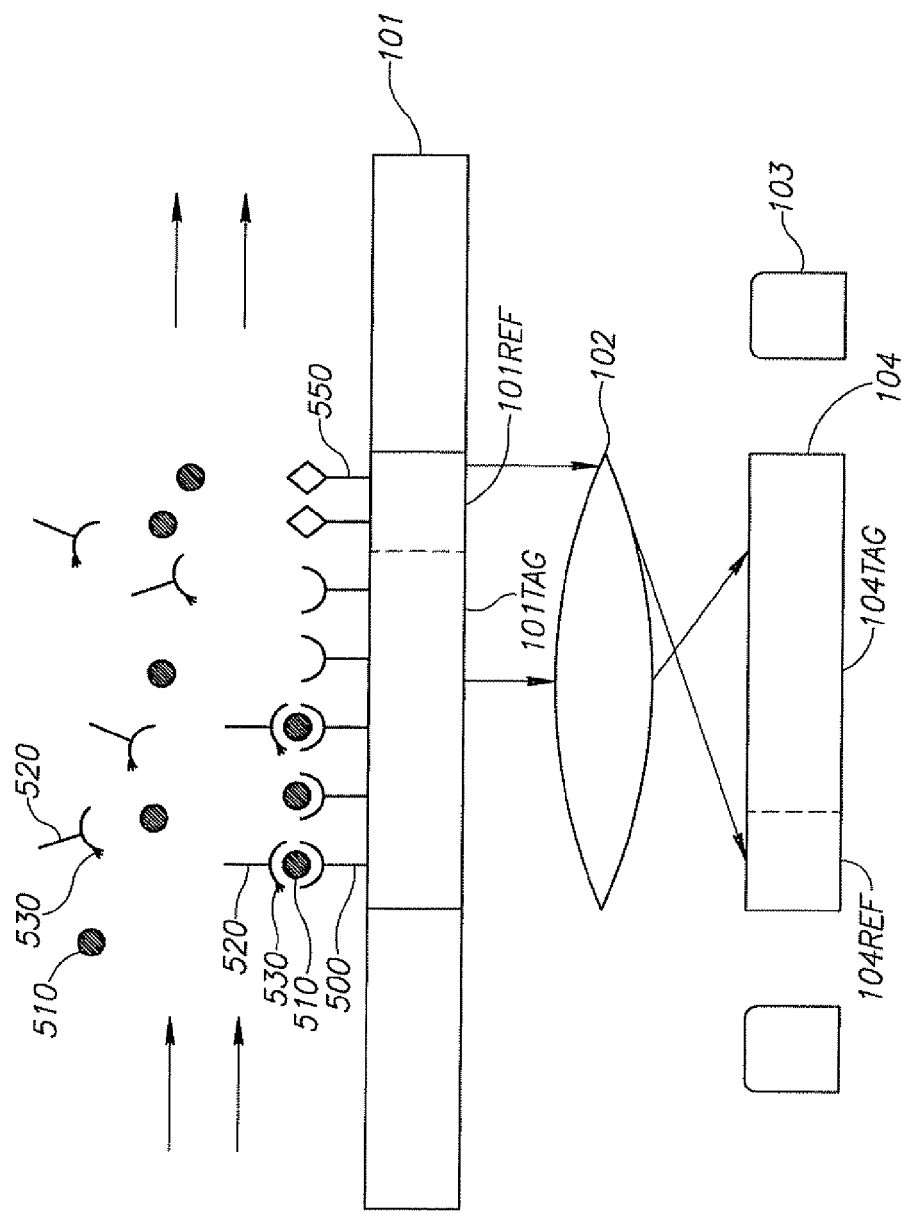
FIG. 5B is a schematic illustration of a reacting layer included in an in-vivo sensing device in accordance with an embodiment of the invention.

Reference is now made to FIG. 5B which is a schematic illustration of a reacting layer included in an in-vivo sensing device in accordance with an embodiment of the invention. According to FIG. 5B, reacting layer 101 may include two separate areas 101TAG and 101REF. As discussed below, areas 101TAG and 101REF are used as active and control regions, respectively, for interpreting the fluorescence emitted by reacting layer 101 and detected by sensor 104.

According to some embodiments, area 101TAG may comprise binding agents 500 attached onto reacting layer 101. Markers 510, which may flow in-vivo, may bind to the binding agents 500 which are specific or with high affinity to marker 510. In order to detect an optical change, binding agents 520, which comprise tag 530, may also have high affinity to marker 510. Binding agents 520 may be inserted in-vivo and may then bind to marker 510. According to some embodiments, area 101REF may comprise reference molecules 550 which not only don't have an affinity to markers 510 but also prevent binding of markers 510 to them. For example, if the markers 510 contain a positive electrical charge, the reference molecules 550 may also contain positive electrical charge in order to "repel" the markers 510. If the markers 510 contain a negative electrical charge, the reference molecules 550 may contain negative charge in order to "repel" the markers 510. Another method of preventing binding between the reference molecules 550 and the markers 510 may be by attaching blocking reagents to the reference molecules 550. Blocking reagents may prevent binding of markers 510 (and maybe of other particles flowing in-vivo as well) to reference molecules 550. According to other embodiments, area 101REF may be free of molecules or binding agents of any kind, such that no substantial binding is to take place in this area.

Sensor 104, which may be an imager, may comprise two areas correlating to the two areas of reacting layer 101. One area may be 104TAG, which may detect optical changes occurring at 101TAG area, i.e., optical changes of the binding agents that are intended to bind to markers 510. Sensor 104 may further comprise area 104REF, which may detect optical changes occurring at 101REF area, i.e., optical changes of the reference molecules 550 that prevent binding of markers 510. According to some embodiments, the reference molecules 550 are used for determining whether the fluorescent signal detected by the sensor 104 indicates specific binding between the binding agents 500 and the marker 510 or whether it is merely fluorescent signals emitted from the in-vivo fluids flowing in proximity to the reacting layer 101. Since the freely flowing in-vivo fluids comprise tagged binding agents 520 that are not bound to area 101TAG, fluorescence may be detected from the "background", i.e., the in-vivo fluids, and not only from reacting layer 101.

Therefore there is a need for reference molecules 550 which may assist in distinguishing between these two fluorescent signals. In some embodiments, the fluorescent "image" in area 104REF may be "subtracted" from the fluorescent "images" in area 104TAG. If the remainder fluorescent signal is higher than a predetermined threshold (which may be determined in lab conditions), it can be inferred that the fluorescent signal indicates specific binding between marker 510 and binding agents 500 and 520, which may indicate on the presence of a pathology. If the remainder fluorescent signal is lower than the threshold, it can be inferred that there is no specific binding between the binding agents 500 and 520 and the markers 510, that is, that the fluorescent signals detected by area 104TAG of sensor 104 may have been of fluorescent molecules flowing within the in-vivo fluids but not attached to the reacting layer 101.

In some embodiments, the area 104TAG of sensor 104 may detect a fluorescent signal in grey scale which may be interpreted to a Bit depth between zero to 256, for example. Other Bit depths may be used, for example, 512 or 1024. The area 104REF of sensor 104 may also detect a signal in grey scale which may be interpreted to a Bit depth between the same scales as the 104TAG area. If the Bit depth of 104TAG area is smaller than the Bit depth of 104REF area, then it may be inferred that no binding between binding agents 500 and marker 510 occurred. If the Bit depth of 104TAG area is larger than the Bit depth of 104REF area, their subtraction is compared with a pre-calculated value. If the subtraction is smaller than the pre-calculated value, it can be concluded that no binding occurred between binding agents 500 and marker 510, but rather a fluorescent signal from in-vivo fluids flowing proximate to the reacting layer 101 was detected. However, if the subtraction between the Bit depth of 104TAG area and 104REF area is equal or larger than the pre-calculated value, it can be concluded that marker 510 was bounded to binding agents 500, i.e., pathology is detected. The pre-calculated value may be calculated in laboratory conditions, for example by allowing markers 510 and binding agents attached onto a solid surface to bind in-vitro under certain conditions, e.g., time, temperature, etc. which would simulate in-vivo conditions but without "background" signals, i.e., fluorescent signals from the in-vivo fluids. This value stands for the threshold indicating specific binding between the binding agents 500 and the marker 510. Below the threshold, no binding occurred; equal to or above the threshold, binding occurred.

In some embodiments, reacting layer 101 may comprise more than one type of binding agents 500, and thus may comprise a corresponding number of reference molecules types. Each binding agent may be attached side by side with its reference molecules that may prevent binding of the markers specific to the corresponding binding agents. When more than one type of binding agent is attached onto reacting layer 101, sensor 104 may comprise more than a single reference section and a single binding/tagging section. Instead, each area of reacting layer 101 having attached thereon one type of binding agent and each reference area having attached thereon the corresponding reference molecules to that one type of binding agents may have a corresponding area on sensor 104 which may detect optical changes therefrom.

Figure 6A:
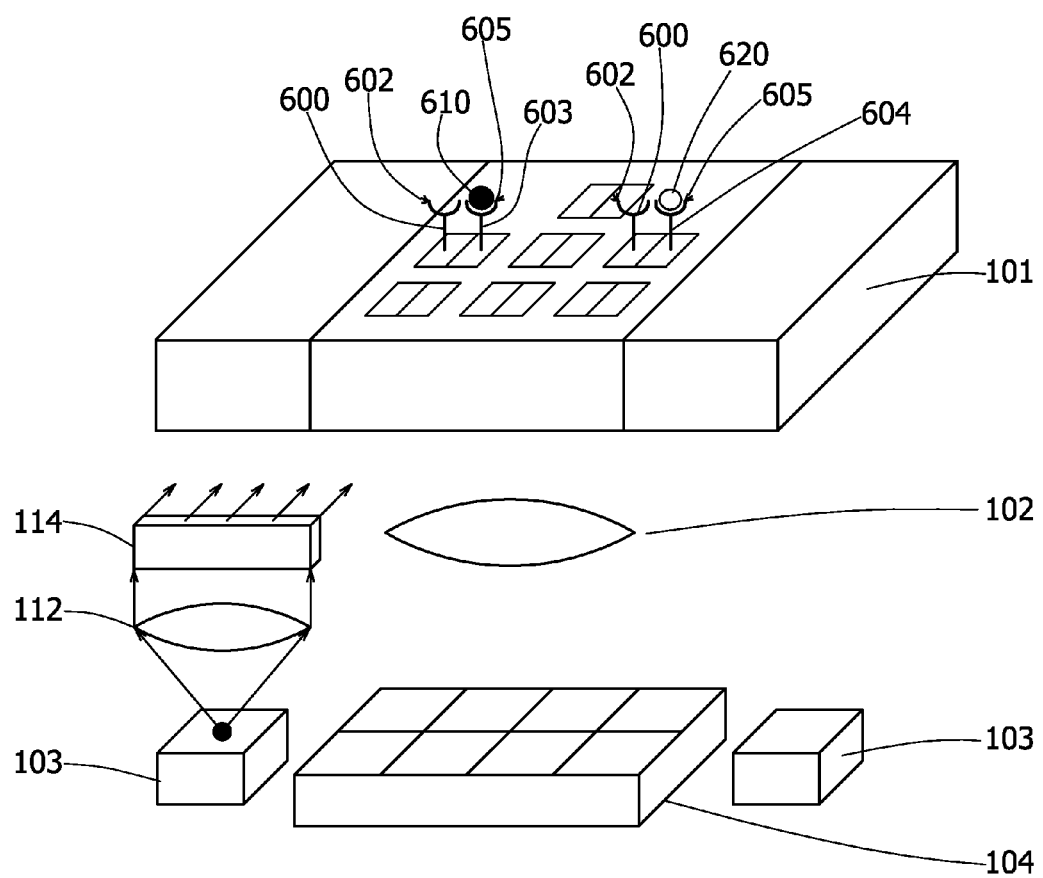
FIG. 6A is a schematic illustration of a reacting layer included in an in-vivo sensing device in accordance with yet another embodiment of the invention.

In other embodiments, as shown in FIG. 6A, reacting layer 101 may be divided into two types of sections. In both sections, there may be attached onto the reacting layer 101 a binding agent 600 specific or with high affinity to both in vivo markers whose ratio is sought. However, in the first type section, in proximate location to the binding agent with high affinity to both markers, is another binding agent 603 specific or with high affinity to only one of the in vivo markers 610. And in the second type section, proximate to the binding agent specific to both markers, is another binding agent 604 but with high affinity only to the other marker 620 different than the marker from the first section type. In some embodiments, binding agent 600 may have a tagging molecule 602 while binding agents 603 and 604 may have a tagging molecule 605, which may be of the same sort or may emit illumination at different spectra.

When an in vivo marker, either 610 or 620 binds to the two binding agents with high affinity to it, the binding agents attached onto the reacting layer 101 acting as a solid phase, go through a conformational change and become closer than they were prior to the binding of the in vivo marker. When the two binding agents are in the new closer position, the two tagging molecules 602 and 605 are then in close proximity to one another, enough to enable "Fluorescence Resonance Energy Transfer" (FRET) when reacting layer 101 is illuminated. Illumination from illumination source 103 may excite one of the tagging molecules 602 to transfer energy to the other tagging molecule 605, so that this second molecule 605 is also excited and emits fluorescence. The fluorescence emitted by the second molecule 605 may be detected by sensor 104, and thus indicate the presence of an in vivo marker.

If an in vivo marker 610 for example, binds at a section not of its type, for example to binding agent 600 which is in proximity to binding agent 605 which is specific to marker 620 (but not to marker 610), FRET would not occur. According to some embodiments, sensor 104 may also be divided into sections correlating to the sections of reacting layer 101. Sensor 104 may detect the various fluorescence exhibited by the tags 605 and, by matching the sections in which illumination was detected or not detected, it can be inferred which of the in vivo markers was actually bound to the binding agents. For example, if, in a section in sensor 104 intended for detecting illumination from marker 610, there was detected illumination, it can be inferred that marker 610 was indeed bound to both binding agents. And if in that same section for marker 610 there was no illumination detected, it can be inferred that marker 620 was the one bound in that section. Summing all of these sections while inferring the presence of either marker 610 or 620 may be used to calculate the ratio between markers, and, by comparing the ratio to a known range indicating pathology, it can be determined whether pathology is present in the body.

In some embodiments, there may be different illumination sources 103 inducing different FRET procedures which may occur on different sections of reacting layer 101. In addition, there may be different fluorescent filters on sensor 104 which correlate to the different sections of reacting layer 101. The filters on sensor 104 may allow transmittance of illumination of specific wavelengths. Such wavelengths may be the wavelength of emission from the second fluorescent molecule participating in FRET. In some embodiments, the wavelength of excitation of the first fluorescent molecule (which is the wavelength illuminated from illumination source(s) 103) and the wavelength of emission from the first fluorescent molecule to the second fluorescent molecule (which is the wavelength of excitation of the second fluorescent molecule) are blocked by the filters on sensor 104, while the wavelength of emission from the second fluorescent molecule is received by sensor 104.

According to FIG. 6A, in some embodiments, in order to collect more light and project it in the most efficient way on reacting layer 101, there may be a condensing lens 112 positioned between reacting layer 101 and illumination source(s) 103, for condensing the illumination emitted from illumination source(s) 103. In some embodiments, there may be an optical system 114 positioned between lens 112 and reacting layer 101. Optical system 114 may be, for example, a prism, for focusing the illumination emitted from illumination source(s) 103 at an angle onto a specific section of reacting layer 101, where a binding agent is attached. In some embodiments, the lens and prism may focus illumination onto a specific section of reacting layer 101, where one of many FRET procedures may be taking place. According to some embodiments, there may be more than one such setting, in which an $i^{th}$ illumination source 103 illuminates an $i^{th}$ section of reacting layer 101, through a condensing lens 112 (and a prism 114). FRET may occur, and the fluorescence emitted by the second fluorescent molecule may be sensed by the $i^{th}$ section in sensor 104.

According to other embodiments, instead of having a setting of illumination source(s) 103 illuminating the different FRET sections on reacting layer 101 simultaneously, each illumination source(s) 103 of the same type only may illuminate reacting layer 101 for a certain period of time. Illumination sources 103 from each type may illuminate synchronously and so according to the wavelength illuminated, the correlating FRET will occur and will accordingly be sensed by the corresponding filter on sensor 104.

According to some embodiments, optical system 102 may be designed so that it focuses illumination emitted from the binding agents attached on reacting layer 101 and does not focus illumination reflected from the surroundings onto sensor 104. This way, illumination from the background will be substantially not detected by sensor 104. In some embodiments, the focal points of sensor 104 should typically be only on the side of reacting layer 101 onto which FRET occurs. When the maximal energy is collected mainly from the distance where FRET occurs and then focused on sensor 104, noise from the in-vivo background may be minimized, so that the signal to noise ratio is maximized.

Figure 6B:
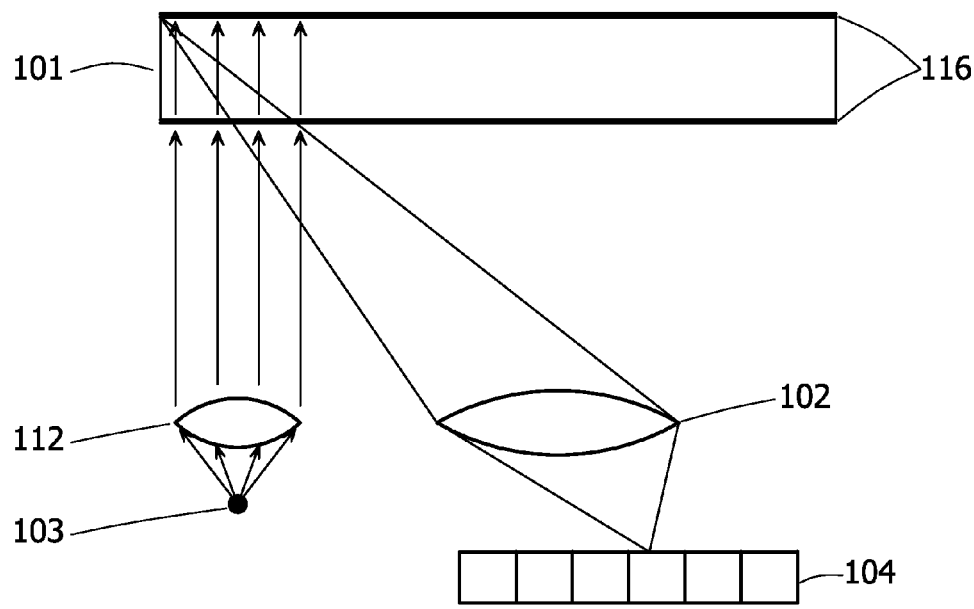
FIG. 6B is a schematic illustration of an optical system in accordance with one embodiment of the present invention.
Figure 6C:
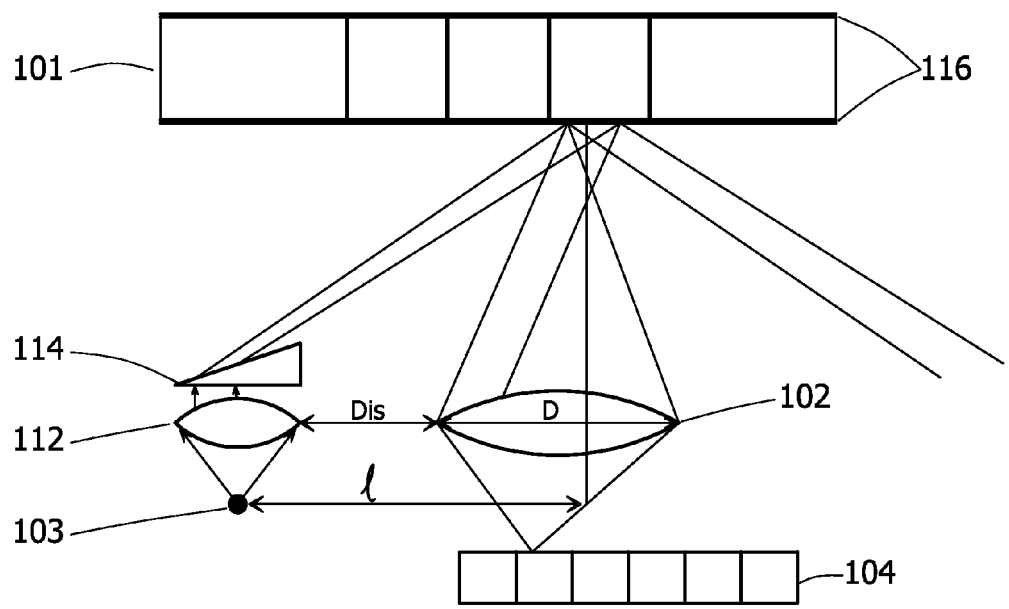
FIG. 6C is a schematic illustration of an optical system in accordance with another embodiment of the present invention.

Reference is now made to FIGS. 6B-6C, which schematically illustrate an optical system according to embodiments of the present invention in which stray light is avoided from entering into the sensor In FIG. 6B, there may be a condensing lens 112 above illumination source(s) 103. Illumination from illumination source(s) 103 may be condensed or collimated by lens 112 onto reacting layer 101, where the binding agents are attached. Illumination emitted from the binding agents in response to FRET, for example, may be focused by optical system 102 onto sensor 104. According to some embodiments, the arrangement of lens 112 in relation to optical system 102 and to reacting layer 101 along with the design requirements of these components may assist in avoiding stray light.

In some embodiments, as a result of use of the condensing lens 112, substantially all of the rays reflected from reacting layer 101 but not from the binding agents are reflected toward illumination source(s) 103 and will not reach sensor 104.

According to some embodiments, there may be more than one section of reacting layer 101 on which more than one FRET procedure may occur, such that there is a need to illuminate only the desired section of reacting layer 101. In FIG. 6C, in addition to condensing lens 112, there may be optical system 114 (for example, a prism), which may shift the angle of illumination to a desired section on reacting layer 101, where FRET may occur. According to some embodiments, the arrangement of lens 112 and optical system 114 in relation to optical system 102 and to reacting layer 101 along with the design requirements of these components may assist in substantially avoiding stray light. According to some embodiments, some of the reflected rays from reacting layer 101 are reflected away from sensor 104. In some embodiments, the condensing lens 112 and prism 114 may be made of refractive optical components. In other embodiments, the lens 112 and prism 114 may be made of diffractive optical components. In some embodiments, as shown in both FIGS. 6B and 6C, there may be an anti-reflective (AR) coating 116, typically on both sides of reacting layer 101, to substantially avoid stray light.

As shown in FIG. 6C, in order to avoid stray light, either one of the following conditions should be kept.

$$21 > Dis + D \quad \text{(i)}$$

or:

$$21 < Dis \quad \text{(ii)}$$

Where "1" is the distance between illumination source 103 and the section of reacting layer 101 on which FRET occurs, on the x axis, "Dis" is the distance between illumination source 103 and lens 102, on the x axis, and D is the diameter of lens 102. FIG. 6C correlates with condition (i), while FIG. 6B correlates with condition (ii). In embodiments which fulfill either one of conditions (i) or (ii), rays reflected from reacting layer 101 but not from the binding agents on it are reflected toward illumination source(s) 103 and will not reach sensor 104. This way stray light is prevented from reaching and being sensed by sensor 104. If neither one of the conditions takes place, then there might be stray light sensed by sensor 104.

Figure 7:
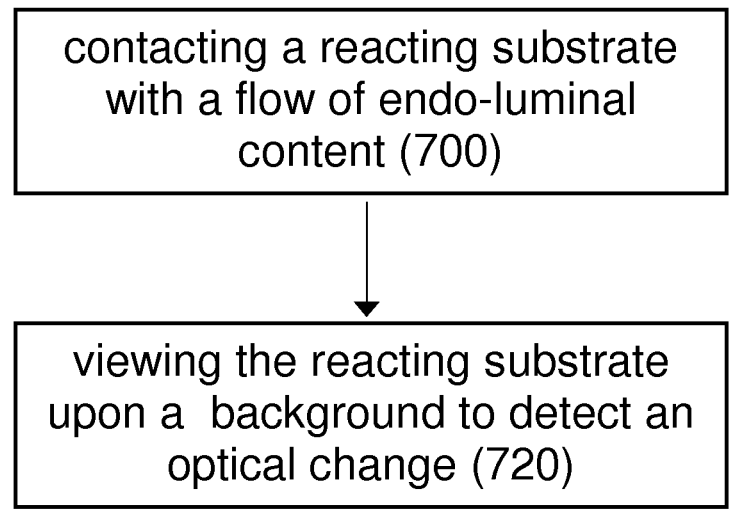
FIG. 7 depicts a method for detecting in-vivo pathology according to an embodiment of the present invention.

Reference is now made to FIG. 7, which depicts a method for detecting in-vivo pathology according to an embodiment of the present invention. According to an embodiment of the invention, as described in FIG. 7, in step 700 a reacting layer is contacted with a flow of endo-luminal content, when according to some embodiments; the reacting layer has at least one type of binding agent attached thereon. According to some embodiments, the reacting layer may be part of an in-vivo device such as device 300 or 400.

In step 720, the reacting layer is viewed to detect an optical change occurring due to binding of a marker in-vivo to the binding agent. According to some embodiments, the reacting layer may be viewed by a sensor such as sensor 104 or image sensor 404. In some embodiments, when an in-vivo marker binds to the binding agent, a structural change of either the binding agent, or the in-vivo marker or both may take place. This structural change may lead to an optical change noticeable when illuminated, and so may be viewed in step 720. The reacting layer is viewed upon a background so as to detect the optical change. According to one embodiment, the background is an opaque cover.

In some embodiments, the reacting layer may have attached thereon two binding agents, each having a fluorescent tagging molecule attached. When the reacting layer is contacted with endo-luminal content, for example, as in step 700, an in vivo marker may bind to the two tagged binding agents. Binding between the in vivo marker and the two binding agents may cause a conformational change which may cause the binding agents to come into close proximity of one another. This may lead to close proximity of the two tagging molecules. Illuminating the reacting layer may excite one of the tagging molecules which may then transfer energy to the second molecule. The second molecule may then exhibit fluorescence which may be viewed upon a background, for example as in step 720. The fluorescence may be sensed at a high signal to noise ratio, since the background isolates the reacting layer from the environment.

In some embodiments, the reacting layer may be part of device 400, and so in addition to detecting the presence of an in vivo marker it may be possible to indicate the location within the lumen of where the marker is present or where it is excreted from into in-vivo fluids flowing inside the lumen, by using image sensor 404. Image sensor 404 may acquire images of the in-vivo lumen that device 400 passes along. According to some embodiments, the images acquired around the same time period as the sensed optical changes may indicate on the in-vivo location of the marker.

Figure 8:
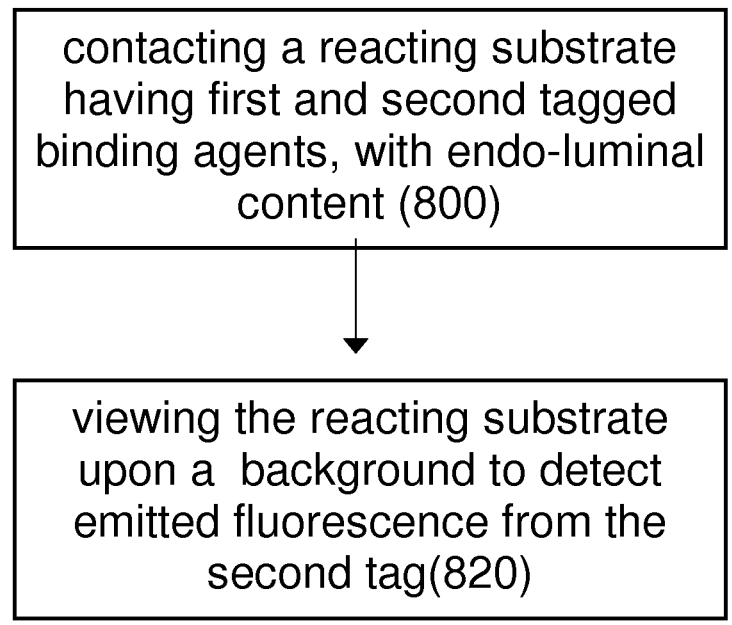
FIG. 8 depicts a method for detecting in-vivo pathology according to another embodiment of the present invention.

Reference is now made to FIG. 8, which depicts a method for detecting in-vivo pathology according to another embodiment of the present invention. According to an embodiment of the invention, as described in FIG. 8, in step 800 an in-vivo sensing device is inserted into a lumen. According to some embodiments, the in-vivo device inserted may be device 300 or device 400. In some embodiments, the in vivo sensing device may comprise a reacting layer, such as reacting layer 101, which has attached thereon two binding agents. The first and second binding agents have attached thereon a first and second tagging molecule, which are typically fluorescent molecules. In step 820, the reacting layer is viewed upon a background to detect fluorescence emitted from the second fluorescent molecule, which indicates binding of an in-vivo marker to the first and second binding agents.

When the reacting layer is contacted with endo-luminal content, for example, as in step 800, an in vivo marker may bind to the two tagged binding agents. Binding between the in vivo marker and the two binding agents may cause a conformational change which may cause the binding agents to come into close proximity of one another. This may lead to close proximity of the two fluorescent molecules. Illuminating the reacting layer may excite the first fluorescent molecule, which may then transfer energy to the second fluorescent molecule. The second molecule may then exhibit fluorescence, which may be viewed upon a background, for example as in step 820. The fluorescence may be sensed at a high signal to noise ratio, since the background isolates the reacting layer from the environment.

If an optical change occurring due do binding of an in-vivo marker to the binding agent is viewed, then there is an indication of the presence of an in-vivo marker sought, which indicates pathology present in-vivo. In some embodiments, when two types of binding agents are attached onto reacting layer 101, the ratio between concentrations of two markers is sought. A ratio between two markers may also be measured by using FRET, for example, as described in FIG. 6A.

Some embodiments of the present invention describe methods for detecting markers present in in-vivo fluids. Such markers may be excreted from cells. Abnormal or over expression of certain markers may indicate pathology, and detection of those markers may assist in diagnosing and treating the pathology.

Figure 9:
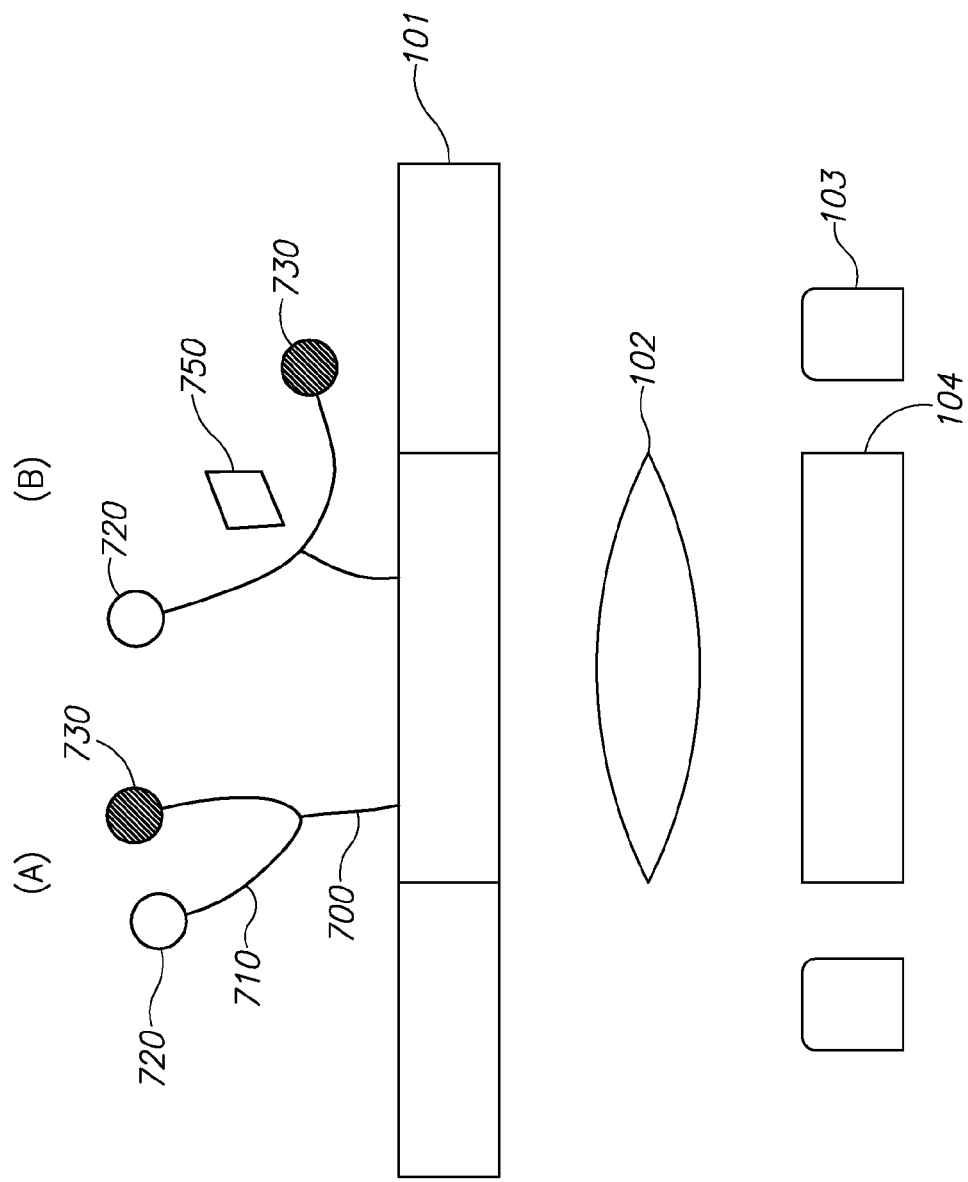
FIG. 9 provides a schematic illustration of a reacting layer included in an in-vivo sensing device in accordance with one embodiment of the invention.

Reference is now made to FIG. 9, which provides a schematic illustration of a reacting layer included in an in-vivo sensing device in accordance with one embodiment of the invention. According to one embodiment, the in vivo sensing device is a swallowable imaging capsule. According to some embodiments, the in vivo sensing device may be, for example, either one of devices 100, 200, 300 and 400, as described hereinabove. According to an embodiment of the invention, as shown in FIG. 9, reacting layer 101 has attached thereon a binding agent 710. In some embodiments, the binding agent 710 may be attached to reacting layer 101 through a spacer 700. According to some embodiments, spacer 700 may be, for example polyethylene glycol (PEG) of different lengths. According to other embodiments, binding agent 710 is attached to reacting layer 101 without a spacer.

According to some embodiments, binding agent 710 may have attached thereon a fluorophore 720 and a quencher 730. In its initial conformation, (A), binding agent 710 may be in a conformation such that fluorophore 720 and quencher 730 are proximate to one another. Proximity between the quencher 730 to fluorophore 720 may lead to inhibition of fluorescence.

When marker 750 binds to binding agent 710, binding agent 710 may undergo a conformational change, (B), which draws quencher 730 apart from fluorophore 720. Such conformational change may lead to fluorescence emission when reacting layer 101 is illuminated by illumination sources 103.

In some embodiments, for example, binding agent 710 may be an oligonucleotide which typically has a loop conformation. A fluorophore 720 may be attached to one end of the loop, while a quencher 730 may be attached to the other end of the loop. When in a loop conformation, fluorophore 720 and quencher 730 are proximate to each other such that fluorescence is inhibited. Following binding of marker 750 to binding agent 710, the loop conformation is changed such that fluorophore 720 and quencher 730 are drawn apart and fluorescence may be exhibited.

In other embodiments, binding agent 710 need not be an oligonucleotide but may be a protein which may bind to a marker 750 or to a target molecule included in marker 750. In some embodiments, the initial conformation of binding agent 710 need not be a loop. According to some embodiments, binding agent 710 may be in any conformation which may initially enable high proximity between a fluorophore 720 and a quencher 730, and, following binding of marker 750, enable quencher 730 to distant from fluorophore 720.

Marker 750 may be excreted into in vivo fluids, which the in vivo sensing device may be passing through. Such excreted markers may include Pepsinogen I/II, MMP-7, CEA, Gastrin 17, Buforin, Cytokeratin 8-CK8, AMP18/gastrokine 1, CA19-9, CA 72-4 and Reg IV, which are proteins typically found in gastric juice. Other markers may include underglycosilated MUCIN-1, CEA and MMP-7, which are typically found in the colon fluids.

Figure 10A:
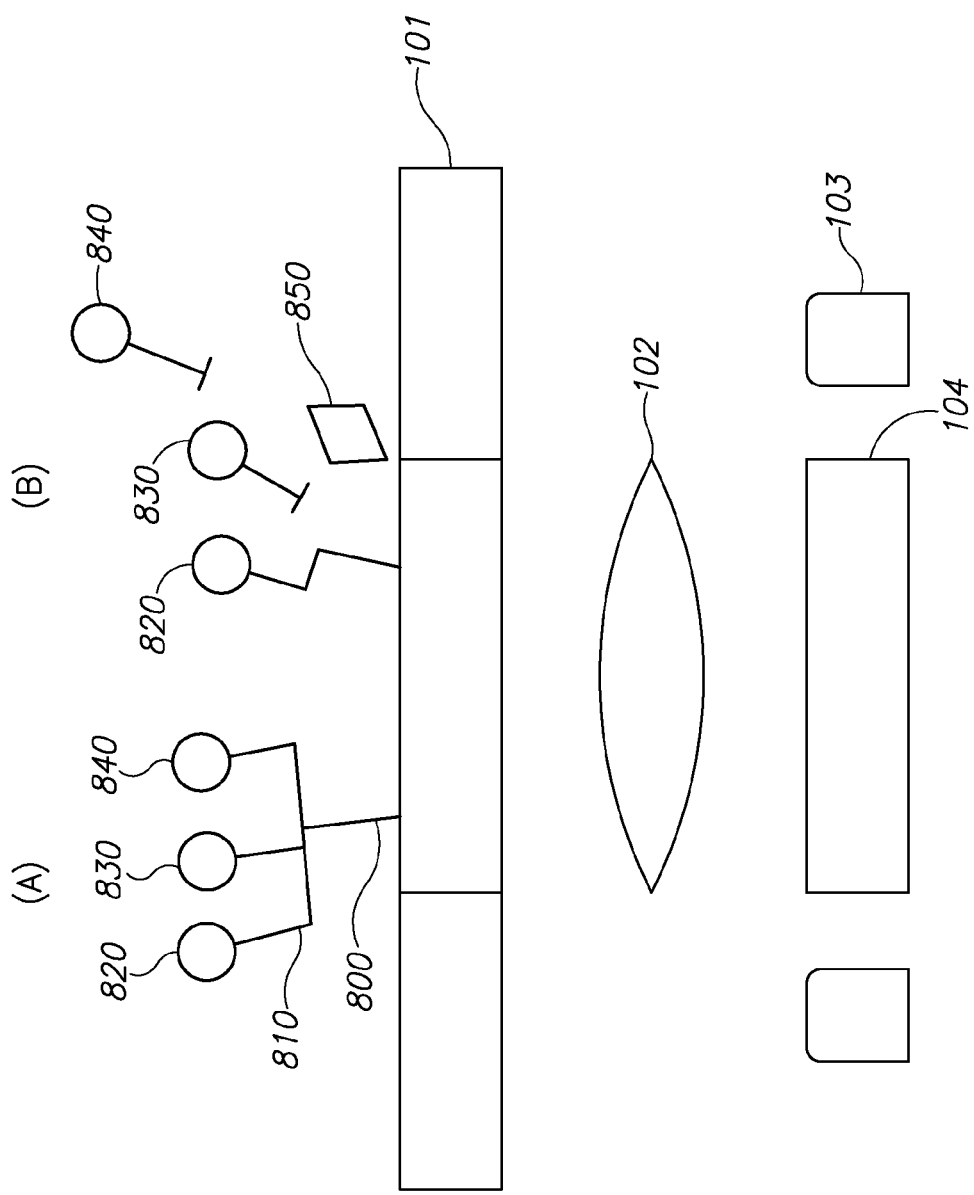
FIGS. 10A and 10B provide a schematic illustration of a reacting layer included in an in-vivo sensing device in accordance with another embodiment of the invention.

Reference is now made to FIG. 10A, which provides a schematic illustration of a reacting layer included in an in-vivo sensing device in accordance with one embodiment of the invention. According to one embodiment, the in vivo sensing device is a swallowable imaging capsule. According to some embodiments, the in vivo sensing device may be, for example, either one of devices 100, 200, 300 and 400, as described hereinabove. According to an embodiment of the invention, as shown in FIG. 10A, a substrate 810 is attached to reacting layer 101. In some embodiments, substrate 810 is attached to reacting layer 101 through a spacer 800, which may be, for example, PEG. According to other embodiments, a spacer need not be used. According to some embodiments, substrate 810 in its initial conformation (A) has attached thereon at least two fluorophores, for example fluorophores 820, 830 and 840. The fluorophores may be positioned proximate to one another. The proximity between fluorophores 820, 830 and 840 inhibits fluorescence emission from either one of the fluorophores.

In some embodiments, when marker 850 flows through the in vivo sensing device such that it is in contact with reacting layer 101 and substrate 810, it may cause cleavage of substrate 810. Following cleavage of substrate 810(B), some of the fluorophores 820, 830 and 840 separate from substrate 810, while at least one fluorophore is still attached. When, for example, fluorophores 830 and 840 separate and draw apart from substrate 810, they may no longer inhibit fluorescence emission from fluorophore 820 still attached to substrate 810.

According to some embodiments, when illumination source(s) 103 illuminate reacting layer 101, the fluorophore that is still attached to substrate 810, for example fluorophore 820, may exhibit fluorescence which may be sensed by sensor 104. In some embodiments, the fluorescence of the released fluorophores 830 and 840 may also be detected by sensor 104. In some embodiments, fluorophores 830 and 840 may still be flowing within the in-vivo sensing device after they are separated from substrate 810, such that they may be sensed by sensor 104 and so enhance the fluorescence signal.

According to some embodiments, there may be different substrates 810 attached onto reacting layer 101 creating an array of substrates on reacting layer 101. The substrates 810 may differ from one another by the fluorophores attached to them. Each section of the array of substrates 810 may have attached thereon fluorophores which differ from one another. In some embodiments, the reacting layer 101 sections may have different fluorophores which emit fluorescence in response to a different wavelength illuminated on them. In other embodiments, each section of reacting layer 101 may differ in the different fluorescent wavelength emitted from the fluorophores attached to it.

In some embodiments, there may be more than one illumination source(s) 103, which may illuminate the reacting layer 101 array in various bandwidths. In some embodiments, sensor 104 may comprise an array of light sensors. Each section in the light sensor array 104 may correlate to a section in the reacting layer 101 array of different substrates. The array of light sensors 104 may correlate to the reacting layer 101 array such that fluorescence emitted from a substrate 810 attached to a section of reacting layer 101 may be sensed in the correlating section of sensor array 104, which may be positioned in line with it and parallel to it. Examining the sensor array 104 and distinguishing which section in the array has sensed fluorescence may indicate the type of in-vivo marker present in-vivo.

According to other embodiments, there may be different substrates 810 attached onto reacting layer 101 creating an array of substrates. The substrates 810 may differ from one another by the in-vivo marker that is designed to cause cleavage from them. In some embodiments, each section of reacting layer 101 is designed to have a high affinity to a different in-vivo marker which may cause cleavage from a specific substrate attached onto it.

According to some embodiments, the marker 850 may be an enzyme. In some embodiments, the substrate 810 may be a protein which may go through enzymatic cleavage by marker 850. The marker 850 may be excreted into in vivo fluids which the in vivo sensing device may be passing through. Such excreted markers may include Pepsinogen I/II and MMP-7.

Figure 10B:
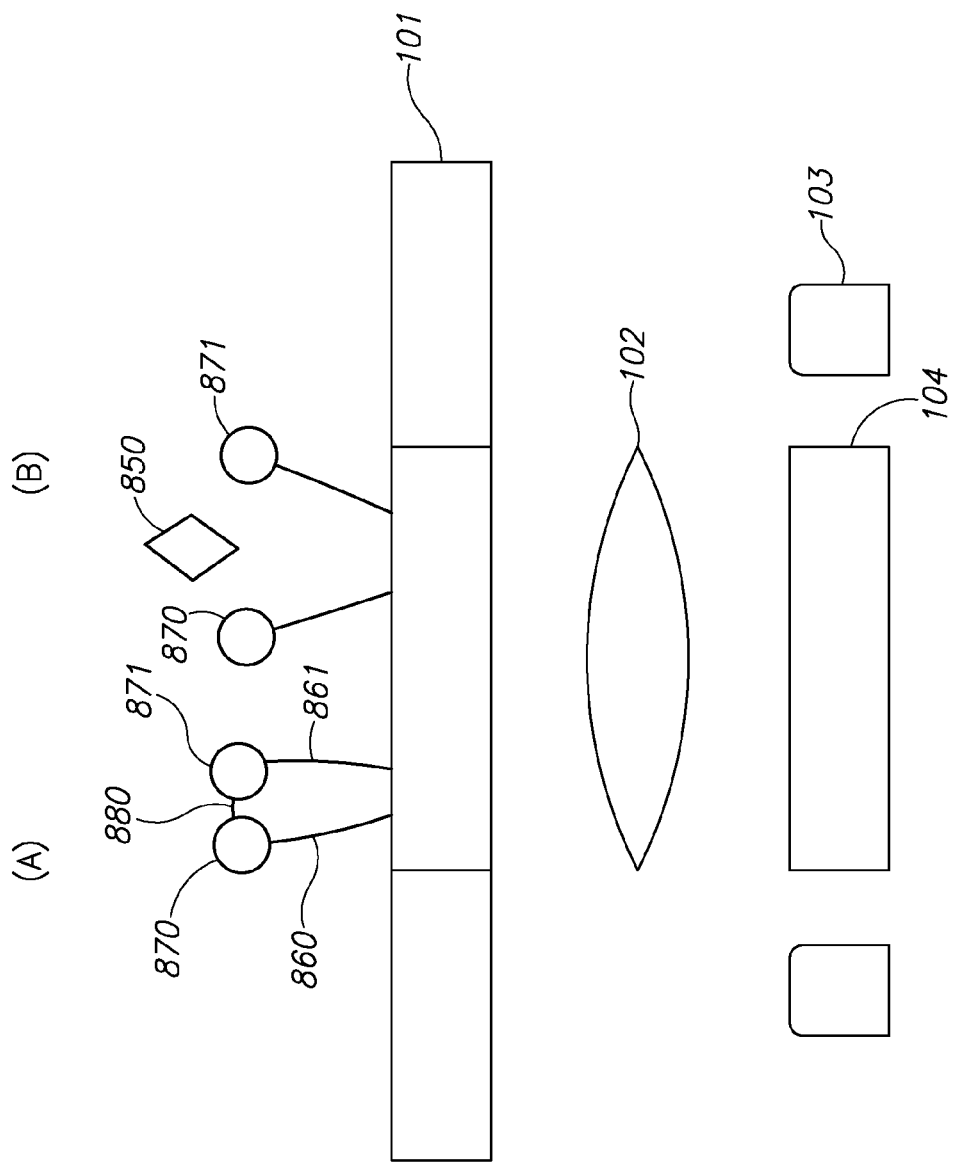

Reference is now made to FIG. 10B, which provides a schematic illustration of a reacting layer included in an in-vivo sensing device in accordance with one embodiment of the invention. According to one embodiment, the in vivo sensing device is a swallowable imaging capsule. According to some embodiments, the in vivo sensing device may be for example, either one of devices 100, 200, 300 and 400, as described hereinabove. According to an embodiment of the invention, as shown in FIG. 10B, reacting layer 101 has attached thereon more than one spacer, for example, spacers 860 and 861. In some embodiments, spacers 860 and 861 may have attached thereon fluorophores 870 and 871, respectively. According to some embodiments, fluorophores 870 and 871 in their initial conformation (A) may be covalently attached through a substrate 880. In some embodiments, in this conformation where fluorophores 870 and 871 are attached to a substrate, they are proximate to one another such that fluorescence is inhibited from either one of fluorophores 870 and 871. According to some embodiments, when marker 850 flows through the in vivo sensing device such that it is in contact with substrate 880, it may cause cleavage of substrate 880. Following cleavage of substrate 880, fluorophores 870 and 871 may be drawn apart so fluorescence may be exhibited (B).

According to some embodiments, instead of more than one fluorophore attached onto reacting layer 101, there may be attached a fluorophore 870 and a quencher 871, such that in the initial conformation (A) fluorophore 870 and quencher 871 may be attached through a substrate 880. In some embodiments, when the fluorophore 870 and quencher 871 are attached through the substrate 880, they may be proximate such that the quencher 871 may inhibit fluorescence emission from the fluorophore 870. After in-vivo marker 850 causes cleavage to substrate 880(B), the quencher 871 is drawn apart from fluorophore 870 so fluorescence may be exhibited and may be sensed by sensor 104.

According to some embodiments, the marker 850 may be an enzyme. In some embodiments, the substrate 880 may be a protein which may go through enzymatic cleavage by marker 850. The marker 850 may be excreted into in vivo fluids which the in vivo sensing device may be passing through. Such excreted markers may include, for example, Pepsinogen I/II and MMP-7.

Figure 11:
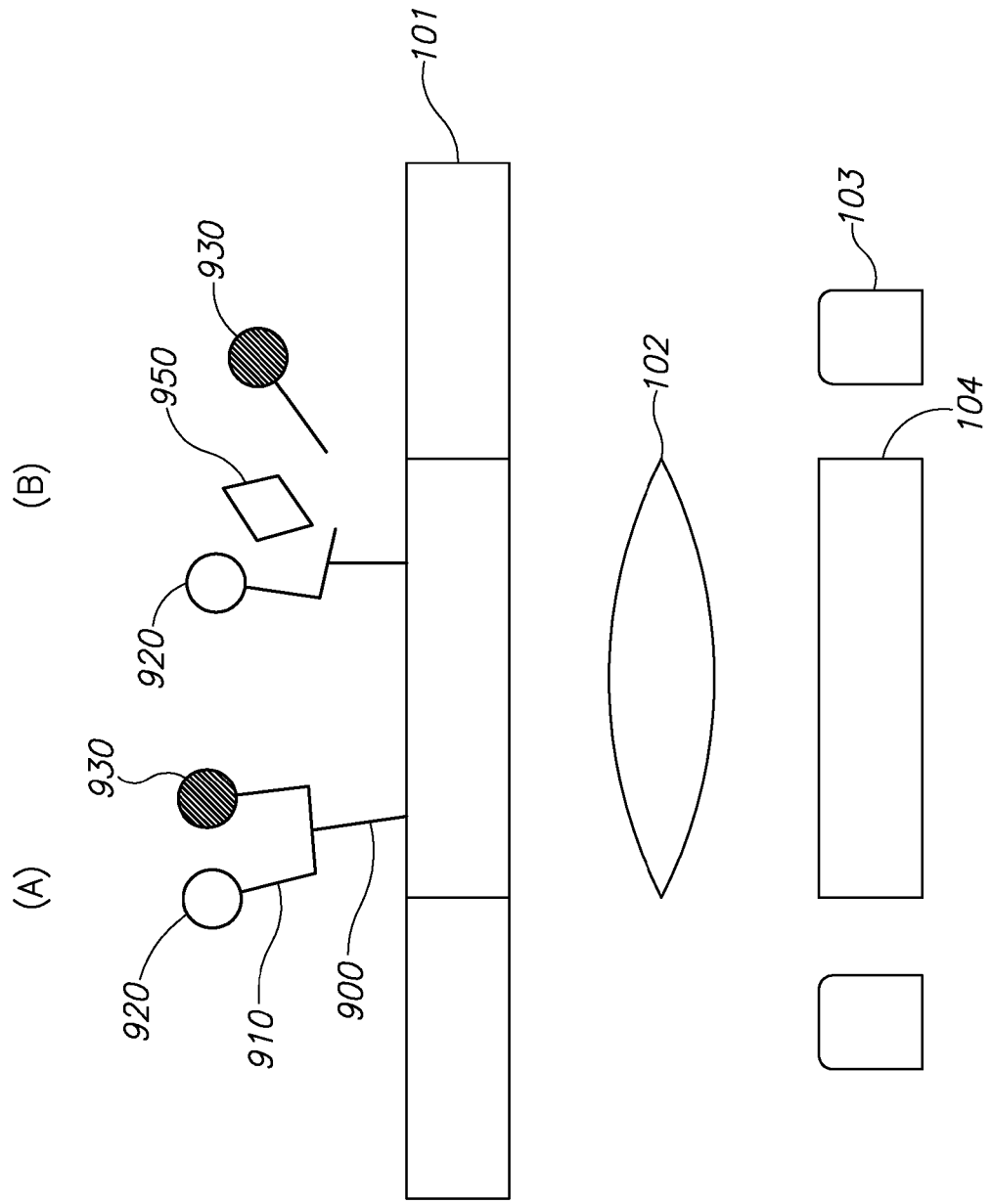
FIG. 11 provides a schematic illustration of a reacting layer included in an in-vivo sensing device in accordance with another embodiment of the invention.

Reference is now made to FIG. 11, which provides a schematic illustration of a reacting layer included in an in-vivo sensing device in accordance with one embodiment of the invention. According to one embodiment, the in vivo sensing device is a swallowable imaging capsule. According to some embodiments, the in vivo sensing device may be for example, either one of devices 100, 200, 300 and 400, as described hereinabove. According to an embodiment of the invention, as shown in FIG. 11, reacting layer 101 has attached thereon a substrate 910. In some embodiments, substrate 910 may be attached to reacting layer 101 through a spacer 900, which may be, for example, PEG.

According to some embodiments, substrate 910 may have attached thereon a fluorophore 920 and a quencher 930. Prior to an interaction between marker 950 and substrate 910, substrate 910 may be in a conformation (A) such that fluorophore 920 and quencher 930 are proximate to one another. High proximity between the quencher 930 to fluorophore 920 may inhibit fluorescence emission. When marker 950 interacts with substrate 910, it may cause cleavage to substrate 910. During cleavage of substrate 910, quencher 930 may be separated from substrate 910(B). Quencher 930 may then be drawn apart from substrate 910 and from fluorophore 920, which is still attached to substrate 910. In some embodiments, the distance between quencher 930 and fluorophore 920 may lead to fluorescence emission from fluorophore 920, when illuminated by illumination source(s) 103.

In some embodiments, quencher 930 may freely flow outside the in vivo sensing device and away from reacting layer 101, along with the continuous flow of in vivo fluids in and out of the in vivo sensing device.

According to some embodiments, the marker 950 may be an enzyme. In some embodiments, the substrate 910 may be a protein which may go through enzymatic cleavage by marker 950. The marker 950 may be excreted into in vivo fluids which the in vivo sensing device may be passing through. Such excreted markers may be Pepsinogen I/II or MMP-7.

A plurality of binding agents, spacers substrates or a combination thereof may be attached onto reacting layer 101, although it may not be illustrated as such in the figures.

Figure 12:
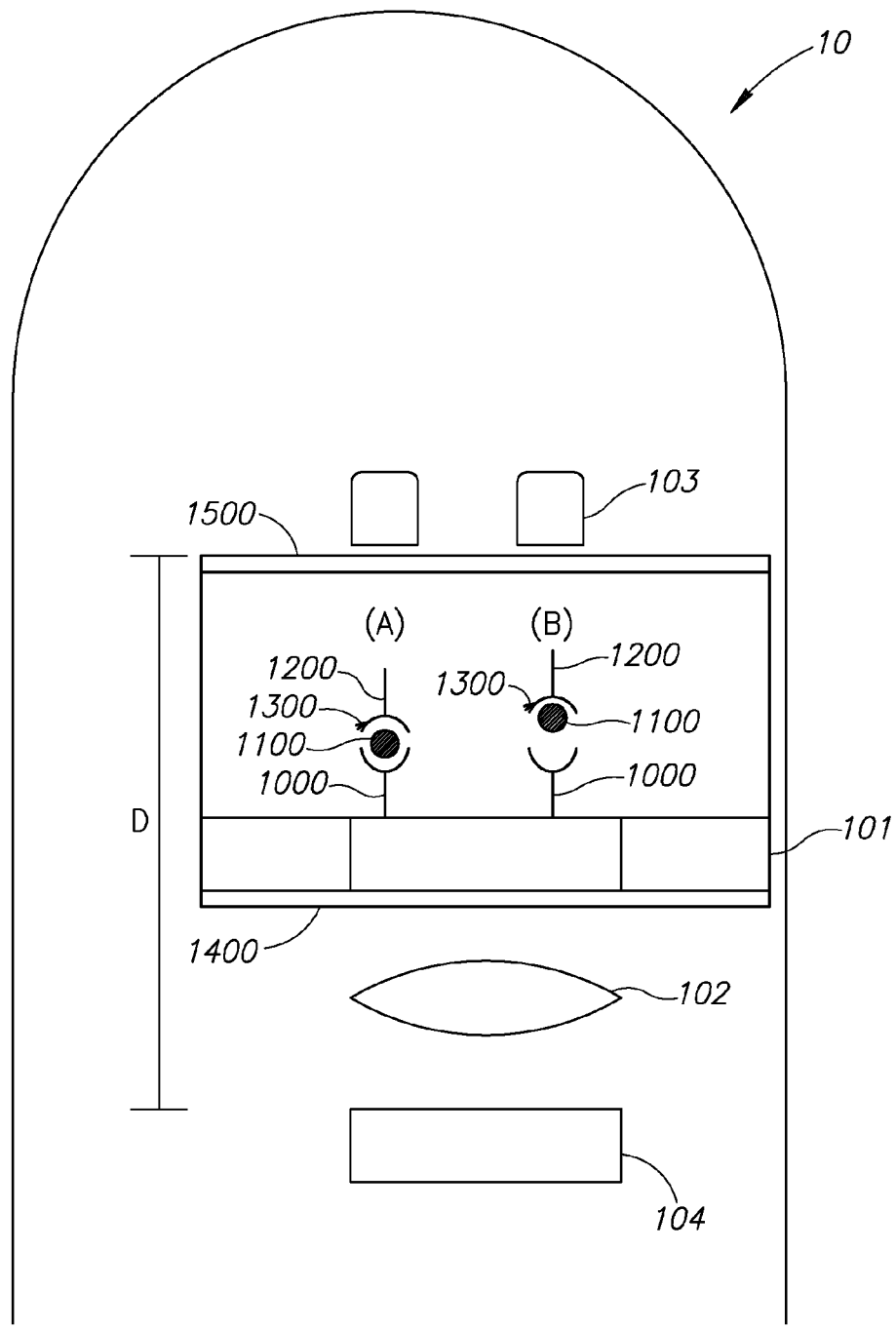
FIG. 12 provides a schematic illustration of an in-vivo sensing device in accordance with one embodiment of the invention, FIG. 13 provides a schematic illustration of a reacting layer included in an in-vivo sensing device in accordance with another embodiment of the invention.

Reference is now made to FIG. 12, which provides a schematic illustration of an in-vivo sensing device 10 in accordance with one embodiment of the invention. According to one embodiment, the in vivo sensing device 10 is a swallowable imaging capsule. According to an embodiment of the invention, as described in FIG. 12, in-vivo device 10 comprises a reacting layer 101 onto which are attached binding agent(s) 1000. Binding agent(s) 1000 are typically specific to or have a high affinity to in-vivo marker 1100. In-vivo device 10 comprises illumination source(s) 103, which illuminates reacting layer 101. In-vivo device 10 further comprises a sensor 104 and optical system 102, which may focus on optical change occurring to binding agent(s) 1000.

According to some embodiments, reacting layer 101 is exposed to in-vivo fluids flowing freely in and out of in-vivo device 10. According to some embodiments, there may be at least one opening through which in-vivo fluids flow. Although FIG. 12 is a two dimensional schematic, it should be appreciated that, according to one embodiment, the opening runs through a cross section of device 10 creating a tunnel-like opening through which fluids may flow. In some embodiments, illumination source(s) 103 are positioned on one wall of the tunnel like opening, whereas reacting layer 101 is positioned on an opposite section of the wall. According to some embodiments, illumination source(s) 103 are positioned on one wall of the opening looking down at reacting layer 101, sensor 104 and optical system 102 which are positioned on the same side as reacting layer 101 and behind it. In some embodiments, the distance between illumination source(s) 103 and sensor 104 (typically the width or height of the tunnel like opening) is approximately between 2-3 mm.

In some embodiments, an in-vivo marker 1100 may flow within the in-vivo fluids flowing continuously through in-vivo device 10. The binding of in-vivo marker 1100 to binding agent 1000 may cause an optical change to occur, which may be sensed by sensor 104. For example, the binding of marker 1100 to binding agent 1000 may cause a conformational change such that an optical change may occur.

In some embodiments, in order to detect the presence of an in-vivo marker 1100 indicating pathology, there may be a need to initiate binding of a tagged binding agent to the marker 1100. According to some embodiments, following binding of the in vivo marker 1100 to the binding agent 1000, which is attached onto reacting layer 101, an additional binding agent 1200, for example an antibody, may be inserted into the body lumen. This inserted binding agent 1200 is typically specific to or has a high affinity to the desired in-vivo marker 1100, typically to a different site on the marker 1100 structure than the site where the binding agent 1000 attached on reacting layer 101 is bound. The inserted binding agent 1200 may be tagged, for example, with gold particles, beads, nanocontainers or a tagging molecule 1300 that may exhibit fluorescence. Other appropriate tagging molecules or methods may be used. Therefore, in some embodiments, following binding of the in vivo marker 1100 to the binding agent 1000 attached to reacting layer 101, the tagged binding agent 1200 may bind to the marker 1100 at a different site, creating a complex (A) of binding agent 1000, marker 1100 and tagged binding agent 1200. When reacting layer 101, onto which the complex is attached, is illuminated, sensor 104 may detect an optical change indicating the different bound molecules and, thus, presence of pathology.

According to some embodiments, the binding agent 1200 inserted into the body lumen, which may be tagged with tagging molecule 1300, may be inserted by drinking, swallowing, injecting or any suitable ways of administration. Typically the insertion of binding agent 1200 is done after a preset time period, following insertion of device 10 into the body. In some embodiments, device 10 may be inserted into the body, and, after a given time period, which may allow binding of the desired in vivo marker 1100 to the binding agent 1000 on reacting layer 101, the tagged binding agent 1200 is inserted into the body.

According to some embodiments, a binding agent 1200 with a tagging molecule 1300 may be inserted into the body lumen prior to the insertion of in-vivo device 10 into the body lumen. Tagged binding agent 1200 may bind to in-vivo marker 1100 flowing in in-vivo fluids, since tagged binding agent 1200 is typically specific to or has a high affinity to the desired in-vivo marker 1100. After a predetermined time period, which may be set such that tagged binding agent 1200 is substantially bound to in-vivo marker 1100, in-vivo device 10 may be administered. The tagged binding agent 1200 and in-vivo marker 1100 may form a complex (B) flowing within in-vivo fluids. This complex may flow through in-vivo device 10 and bind to binding agent 1000 attached to reacting layer 101. Illumination onto reacting layer 101 may cause fluorescence emission, which may be sensed by sensor 104.

In some embodiments, there may be a filter 1400 positioned between reacting layer 101 on one side and optical system 102 and sensor 104 on the other side. Filter 1400 may filter illumination emitted from reacting layer 101 so as to transfer mostly illumination emitted from the complex of binding agent 1000, marker 1100 and tagged binding agent 1200. In some embodiments, illumination emitted from reacting layer 101 may first be filtered by filter 1400 before being sensed by sensor 104. In some embodiments, filter 1400 may filter illumination passing through reacting layer 101 by allowing passage of illumination of a specific predetermined bandwidth. The predetermined bandwidth may be the bandwidth correlating with the optical change occurring on reacting layer 101. Typically, the filter 1400 may allow passage of illumination of a bandwidth unique to the emission from the complex of binding agent 1000, marker 1100 and tagged binding agent 1200.

In some embodiments, a filter 1500 may be positioned between illumination source(s) 103 and reacting layer 101, such that illumination projected from illumination source(s) 103 is first filtered and only then illuminated onto reacting layer 101. Filter 1500 may filter illumination such that only specific bandwidths may pass through and illuminate reacting layer 101. In some embodiments, filter 1500 may filter illumination such that substantially only illumination in the excitation bandwidth, which may excite the complex of binding agent 1000, marker 1100 and tagged binding agent 1200 may pass through filter 1500.

Figure 13:
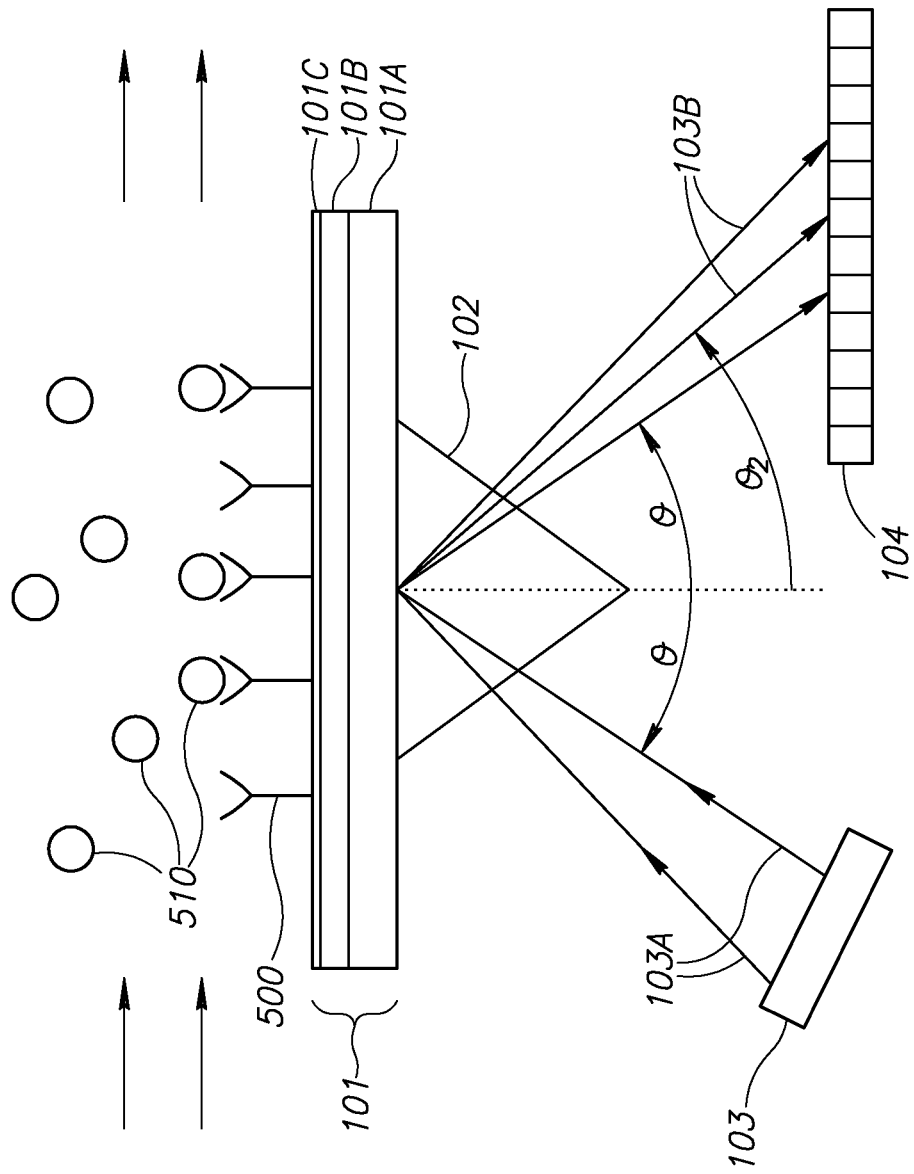

Reference is now made to FIG. 13, which provides a schematic illustration of a reacting layer included in an in-vivo sensing device in accordance with another embodiment of the invention. According to one embodiment, the in vivo sensing device may be a swallowable imaging capsule. According to some embodiments, the in vivo sensing device may be, for example, either one of devices 100, 200, 300, 400 and 10, as described hereinabove. According to an embodiment of the invention, as shown in FIG. 13, the in-vivo sensing device may include a Surface Plasmon Resonance (SPR) measuring system.

According to some embodiments, the in-vivo sensing device may comprise a reacting layer 101 which may include a plurality of layers such as reacting layers 101A, 101B, and 101C. In some embodiments, a different number of reacting layers may be used. According to an embodiment of the present invention, reacting layer 101 has attached thereon binding agents 500. In some embodiments, the binding agents 500 may be immobilized onto reacting layer 101 through hydrogel or a spacer 101C. According to some embodiments, spacer 101C may be, for example, PEG. Non-specific binding of molecules to reacting layer 101 may be reduced by attaching PEG molecules to reacting layer 101. PEG molecules may serve as a steric barrier to prevent undesirable non-specific interactions from occurring on the surface of reacting layer 101, which may increase the signal to noise ratio. According to other embodiments, binding agent 500 is attached onto reacting layer 101 without a spacer.

In some embodiments, reacting layer 101A may be made of glass or plastic, or may be part of the in-vivo sensing device's body and so may be made of the same material from which the device's body is made of. In some embodiments, reacting layer 101B may be made of a metal film, typically a noble metal, for example gold.

According to some embodiments, the in-vivo sensing device may further comprise optical system 102, which may be a hemisphere or prism, an illumination source 103, which typically illuminates visible or infra-red light, and a light sensor 104. In some embodiments, light sensor 104 may be a vector detector.

Figure 14:
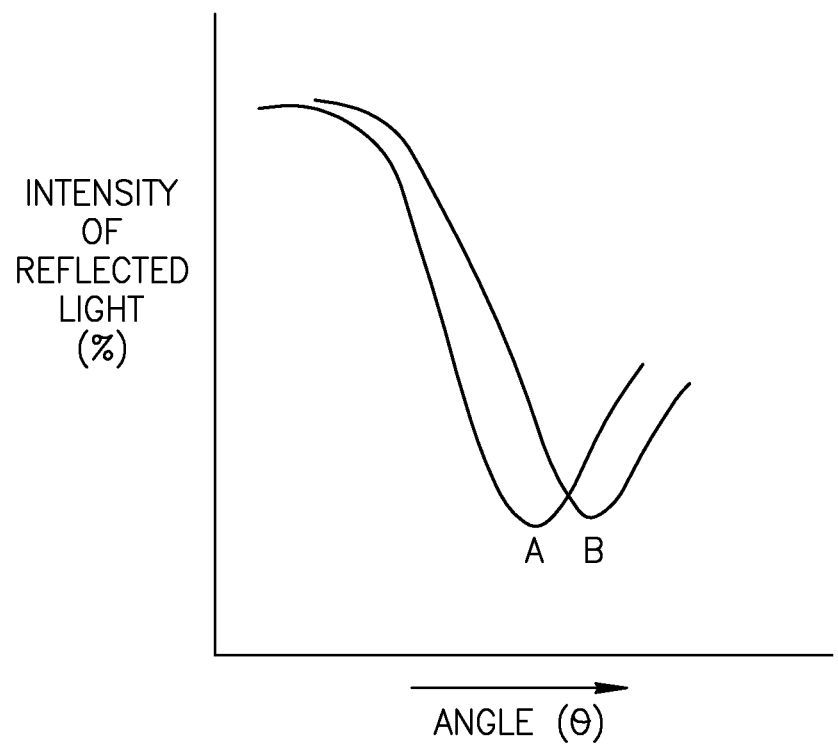
FIG. 14 provides a schematic illustration of a graph in accordance with an embodiment of the invention.

In some embodiments, light 103A from illumination source 103 may pass through prism 102 such that the light impinge reacting layer 101A at a predefined angle θ. At predefined angle θ, some of the light may cause excitation of surface plasmons which results in a decrease in the intensity of reflected light 103B (as shown in FIG. 14 as line A). When marker 510 which freely flows within the in-vivo fluids, binds to binding agent 500, the refractive index of the reacting layer 101B, e.g., the gold film, may be changed, such that it may cause an angle shift from angle θ to angle $θ_2$ (shown in FIG. 14 as line B).

During SPR measurements, the predefined angle θ or SPR angle θ is an angle known to excite surface plasmon in reacting layer 101B and thereby induce surface plasmon resonance. The SPR angle θ is the angle at which a maximum decrease in the intensity of the reflected light occurs. Since SPR is a phenomenon occurring on the surface of a material, it depends on optical properties of the surface of the material. A change of optical properties of that surface, e.g., a change in the refractive indices of the system, may cause a change in the reflected angle. The SPR angle θ depends on the refractive indices of the system at both sides of reacting layer 101B. The refractive index at the prism 102 side (which is one side of reacting layer 101B) is constant, but the refractive index at the side of the reacting layer 101C (which is the other side of reacting layer 101B) may change due to binding of marker 510 to binding agents 500. The refractive index of reacting layer 101B may change due to mass accumulation of marker 510 onto reacting layer 101C. Such a change in the refractive index of reacting layer 101B may cause a change in the conditions under which SPR occurs, and so cause a shift in the SPR angle θ, for example, from θ to shifted angle θ2 (shown in FIG. 14 as line B, which is shifted from line A).

According to some embodiments, angle θ and angle θ2 may be measured by using a vector detector 104. The decrease in the intensity of the reflected light 103b is shifted due to changes in the refractive index of the reacting layer 101C (due to binding of marker 510 to binding agents 500). The angle of that decrease may be detected by the location of whichever pixel of vector detector 104's pixels detected that specific decrease in light reflection intensity. In some embodiments, light sensor 104, which is typically a vector detector, may detect onto which pixel less light was reflected, in comparison to the other pixels. The location of the pixel along the vector detector 104, which detected the decrease in light (or shadow), may indicate the SPR angle. Comparison between the SPR angles throughout the entire passage of the in-vivo sensing device (either one of devices 100, 200, 300, 400 and 10) may indicate the presence of marker 510 in-vivo.

Figure 15:
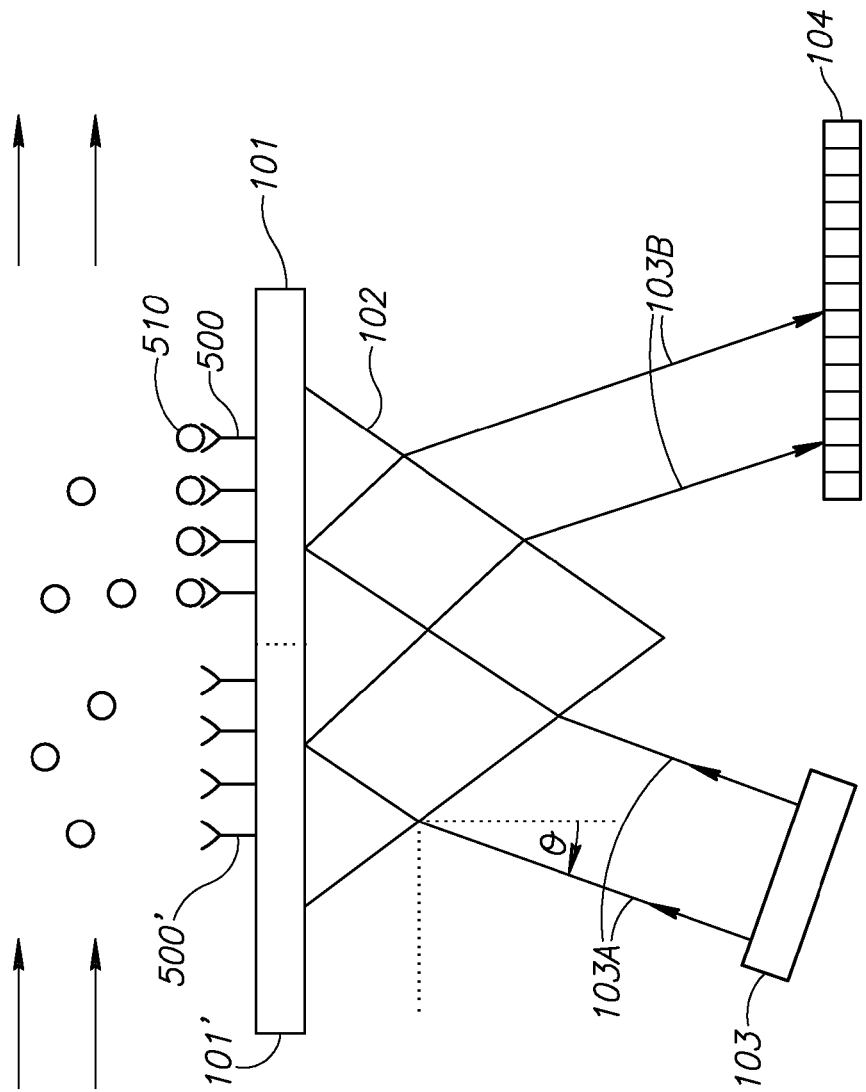
FIG. 15 provides a schematic illustration of a reacting layer included in an in-vivo sensing device in accordance with yet another embodiment of the present invention.

Reference is now made to FIG. 15, which provides a schematic illustration of a reacting layer included in an in-vivo sensing device in accordance with yet another embodiment of the invention. According to one embodiment, the in vivo sensing device may be a swallowable imaging capsule. According to some embodiments, the in vivo sensing device may be, for example, either one of devices 100, 200, 300, 400 and 10, as described hereinabove. According to an embodiment of the invention, as shown in FIG. 15, the in-vivo sensing device may include a Surface Plasmon Resonance (SPR) measuring system.

In some embodiments, during passage of the in-vivo sensing device throughout the GI tract, in-vivo fluids freely flow through the openings of the device's opaque cover (or reference background). The in-vivo fluids may carry various particles within it, e.g., turbid media, and thus change the refractive index of reacting layer 101. In some embodiments, reacting layer 101 may include a plurality of layers such as reacting layers 101A, 101B, and 101C, as shown in FIG. 13. In some embodiments, reacting layer 101 may further comprise a reference section 101'. Such a reference section 101' may either be free of binding agents 500 or may have attached thereon "anti-binding agents" 500', so as to ensure no binding of marker 510 onto the reference section 101'. For example, the reference section 101' may comprise reference molecules that "repel" the marker 510. If marker 510 has a positive electrical charge, the reference molecules may also comprise a positive electrical charge so as to repel the marker 510 from binding to the reference molecules. Another example of molecules that "repel" the marker 510 may include reference molecules having attached thereon a blocking reagent that block binding of particles to it.

The reference section 101' along with the other section of reacting layer 101, may be illuminated through illumination source 103 at a predefined angle θ (shown as light rays 103A), and the intensity of the reflected light 103b may be measured. Comparison between the intensity of light reflected from the reference section 101' (e.g., from binding agents 500') and the intensity of light reflected from the section onto which binding agents 500 are attached may provide a more accurate indication as to whether or not the marker 510 is present in-vivo. Such a comparison may indicate whether the change in the refractive index of reacting layer 101 is due to the various particles flowing in proximity to reacting layer 101 but which are not bound to reacting layer 101, or whether it is due to binding of marker 510 to binding agents 500.

According to some embodiments, an SPR measuring system may be used to determine whether marker 510 is bound to binding agent 500. In some embodiments, when using SPR to determine the presence of marker 510, marker 510 is typically free of tagging molecules of any kind. That is, marker 510 which freely flows within the in-vivo fluids is not bound to any tagging molecule, such as gold particles, beads, or fluorescence emitting molecule of any kind. If a shift in the SPR angle is measured, that shift may be an indication of the presence of marker 510 in-vivo, and so may indicate on the presence of a pathology in-vivo.

In some embodiments, as shown in FIG. 15, binding agents 500 may be attached onto reacting layer 101 side by side with reference molecules 500'. In some embodiments, each of the binding agents 500 and the reference molecules 500' may comprise a matrix of binding agents 500 and reference molecules 500', respectively. When the reacting layer's sections are positioned side by side, a single-row vector detector 104 may be suitable for detecting the angle and the angle shift of reflected illumination from each reacting layer's section (as shown in FIG. 15). However, other reacting layer 101 configurations may require other vector detector 104 configurations. For example, if the reacting layer's sections are positioned one on top of the other (i.e., turned at 90 degrees to the configuration shown in FIG. 15), then a two-row vector detector 104 may be used. Each row of the vector detector 104 may detect and angle shift from one of the rows of the reacting layer 101, either the reference section 101' or the section onto which binding agents 500 are attached.

According to some embodiments, the SPR measuring system implemented in any of the different in-vivo sensing devices described in this invention (e.g., sensing devices 100, 200, 300, 400 or 10) may be an SPR system as described in FIG. 13 or FIG. 15. According to other embodiments, other SPR measuring systems may be used.

It will be appreciated that the present invention is not limited to what has been particularly shown and described hereinabove. Rather the scope of the present invention is defined only by the claims which follow.

What is claimed is:

1. An in-vivo sensing device for detecting in-vivo pathology comprising:
    a device body enclosing:
        a reacting layer having at least one type of binding agent attached thereon;
        a sensor configured to sense an optical change on said reacting layer; and
        at least one illumination source configured to illuminate said reacting layer;
        each of said sensor and illumination source facing in a forward direction towards said reacting layer such that rays from the illumination source impinge on the reacting layer and are then emitted to the sensor;

wherein the device body comprises at least two openings forward of the reacting layer to allow in vivo fluids to flow through said device body and over said reacting layer.

2. The device according to claim 1, wherein the optical change is selected from the group consisting of: a change of color, a change of hue, a change of brightness, a change of optical density, a change of transparency, a change of light scattering, and any combination thereof.

3. The device according to claim 1, wherein said at least one illumination source comprises a white LED.

4. The device according to claim 1, wherein said at least one illumination source comprises a monochromatic illumination source.

5. The device according to claim 1, further comprising more than one illumination source, wherein each of the more than one illumination source has a different illumination spectra.

6. The in-vivo sensing device according to claim 1, wherein said reacting layer includes a substance selected from the group consisting of: silicon, glass, and plastic.

7. The in-vivo sensing device according to claim 1, wherein said reacting layer is positioned at an end of the device body, perpendicular to the forward sensing direction.

8. The device according to claim 1, wherein said openings are shaped so as to induce continuous flow of fluids in and out of the device body.

9. The device according to claim 1, wherein said device body comprises a reference background positioned over said reacting layer.

10. The device according to claim 9, wherein said reference background comprises a mirror.

11. The device according to claim 9, wherein said openings allow in vivo fluids to flow through and beneath said reference background.

12. The device according to claim 1, wherein said sensor comprises an array of light sensitive elements having differing spectrum sensitivities.

13. The device according to claim 1, wherein said device is a swallowable capsule.

14. A method for detecting in vivo pathology comprising the steps of:

administering an in vivo sensing device comprising a sensor, an illumination source, a reacting layer and a background, each of said sensor and illumination source facing in a forward direction towards said reacting layer;

contacting the reacting layer having at least one type of binding agent attached thereon with a flow of endoluminal content forward of the reacting layer;

illuminating the reacting layer upon the background; and sensing an optical change occurring due to binding of the binding agent to a marker in vivo.

15. The method according to claim 14, where said in-vivo marker is excreted from an in-vivo lumen into in-vivo fluids flowing inside a lumen.

16. The method according to claim 14, further comprising administering to a patient a binding agent with a tag, wherein said tagged binding agent has an affinity for the marker when it is bound to the binding agent.

17. The method according to claim 16, wherein said tag is selected from the group consisting of gold particles, beads, nano-containers, and fluorescence emitting molecules.

* * * * *